US007879545B2

(12) United States Patent
Torres-Roca et al.

(10) Patent No.: US 7,879,545 B2
(45) Date of Patent: Feb. 1, 2011

(54) IDENTIFICATION OF NOVEL TARGETS FOR RADIO SENSITIZATION USING A GENOMIC-BASED RADIATION SENSITIVITY CLASSIFIER

(75) Inventors: Javier F. Torres-Roca, St. Petersburg, FL (US); Timothy Yeatman, Tampa, FL (US); Steven Eschrich, Lakeland, FL (US)

(73) Assignees: H. Lee Moffitt Cancer Center and Research Institute, Inc., Tampa, FL (US); University of South Florida, Tampa, FL (US)

( * ) Notice: Subject to any disclaimer, the term of this patent is extended or adjusted under 35 U.S.C. 154(b) by 65 days.

(21) Appl. No.: 10/904,326

(22) Filed: Nov. 4, 2004

(65) Prior Publication Data

US 2005/0123945 A1 Jun. 9, 2005

Related U.S. Application Data

(60) Provisional application No. 60/481,604, filed on Nov. 5, 2003.

(51) Int. Cl.
*C12Q 1/68* (2006.01)
*G01N 33/53* (2006.01)
(52) U.S. Cl. .................. 435/6; 435/4; 436/57; 436/58; 536/23.1
(58) Field of Classification Search ..................... 435/6, 435/4; 436/57, 58; 536/23.1
See application file for complete search history.

(56) References Cited

U.S. PATENT DOCUMENTS

| | | | |
|---|---|---|---|
| 6,100,243 | A | 8/2000 | Frisch |
| 6,342,217 | B1 | 1/2002 | Link et al. |
| 2002/0128220 | A1 | 9/2002 | Gleave et al. |
| 2003/0175717 | A1 | 9/2003 | Li et al. |
| 2005/0123945 | A1 | 6/2005 | Torres-Roca et al. |
| 2005/0282766 | A1 | 12/2005 | Wu et al. |

FOREIGN PATENT DOCUMENTS

WO  WO00/50643  *  8/2000

OTHER PUBLICATIONS

Virginia Goss Tusher et al., Significance analysis of microarrays applied to the ionizing radiation response. PNAS 2001, 98(9), 5116-5121, Apr. 24, 2001.*

Thomas Bork-Eriksson, et al, Tumor Radiosensitivity is a prognostic factor for local control in head and neck cancers, Int. J. radiation Oncology Biol. Phys., vol. 46, No. 1, pp. 13-19, 2000.*

Hongming Qiu, et al, Molecular Prognostic Factors in Rectal Cancer Treated by Radiation and Surgery, Dis Colon Rectum, vol. 43, No. 4 pp. 451-459, Apr. 2000).*

Javier F. Torres-Roca, et al., Predicton of Radiation Sensitivity using a Gene Expression Classifier, Cancer Res; 65: (16), 7169-7176, Aug. 15, 2005.*

Khan et al, Nature Medicine, 7,(60, Jun. 2001, 673-679.*

Potti, A., et al. Genomic signatures to guide the use of chemotherapeutics. (2006). Nat Med 12(11):1294-1300.

Pramana, J., et al. Gene expression profiling to predict outcome after chemoradiation in head and neck cancer. (2007) Int J Radiat Oncol Biol Phys 69(5):1544-1552.

R Development Core Team. R: A language and environment for statistical computing. (2008) In: R Foundation for Statistical Computing. Vienna.

Reboul, F., Radiotherapy and chemotherapy in locally advanced non-small cell lung cancer: preclinical and early clinical data. (2004). Hematol Oncol Clin North Am 18:41-53.

Rich, T. A., et al. Preoperative infusional chemoradiation therapy for stage T3 rectal cancer. (1995). International journal of radiation oncology, biology, physics 32(4):1025-1029.

Rose, P. G., et al. Concurrent Cisplatin-Based Radiotherapy and Chemotherapy for Locally Advanced Cervical Cancer. (1999). N. Engl J Med 340:1144-1153.

Rosen, E. M., Biological Basis of Radiation Sensitivity. Part 2: Cellular and Molecular Determinants of Radiosensitivity. (2000). Oncology (Williston Park) 14:741-757.

Russell, J. S., et al. Gleevec-Mediated Inhibition of Rad51 Expression and Enhancement of Tumor Cell Radiosensitivity. (2003). Cancer Res 63:7377-7383.

Sauer, R., et al. Preoperative versus postoperative chemoradiotherapy for rectal cancer. (2004) N Engl J Med 351 (17):1731-1740.

Schaake-Koning, C., et al. Effects of concomitant cisplatin and radiotherapy on inoperable non-small-cell lung cancer. (1992). N Engl J Med 326:(8)524-530.

(Continued)

*Primary Examiner*—T. D. Wessendorf
(74) *Attorney, Agent, or Firm*—Robert Varkonyi; Smith & Hopen, P.A.

(57) ABSTRACT

A classifier to predict cellular radiation sensitivity based on gene expression profiles in thirty-five cell lines from the NCI panel of 60 cancer cell lines (NCI-60), using a novel approach to predictive gene analysis. Three novel genes are provided, retinoblastoma binding protein 4 (RbAp48), G-protein signaling regulator 19 (RGS19) and ribose-5-phosphate isomerase A (R5PIA) whose expression values were correlated with radiation sensitivity.

4 Claims, 15 Drawing Sheets

OTHER PUBLICATIONS

Shedden, K., et al. Gene expression-based survival prediction in lung adenocarcinoma: a multi-site, blinded validation study. (2008) Nat Med 14(8):822-827.

Simon R., et al. Pitfalls in the Use of DNA Microarray Data for Diagnostic and Prognostic Classification. (2003) J Natl Cancer Inst 95(1):14-18.

Staunton, J. E., et al. Chemosensitivity prediction by transcriptional profiling. (2001). Proc Natl Acad Sci U S A 98 (19):10787-10792.

Stausbol-Gron B., et al. Relationship between tumour cell in vitro radiosensitivity and clinical outcome after curative radiotherapy for squamous cell carcinoma of the head and neck. (1999) Radiother Oncol 50:47-55.

Taghian A., et al. Intrinsic radiation sensitivity may not be the major determinant of the poor clinical outcome of glioblastoma multiforme. (1993) Int J Radiat Oncol Biol Phys 25:243-249.

Tannapfel A., et al. Apoptosis, proliferation, bax, bcl-2 and p53 status prior to and after preoperative radiochemotherapy for locally advanced rectal cancer. (1998) Int J Radiat Oncol Biol Phys 41(3):585-591.

Tepper J., et al. Superiority of trimodality therapy to surgery alone in esophageal cancer: Results of CALGB 9781. (2006) Journal of Clinical Oncology 24(18S).

Terzoudi, G. I., et al.. Increased G2 chromosomal radiosensitivity in cancer patients: the role of cdk1/cyclin-B activity level in the mechanisms involved. (2000). Int J Radiat Biol 76(5):607-615.

Zhang, W., et al. FoxO1 regulates multiple metabolic pathways in the liver: effects on gluconeogenic, glycolytic, and lipogenic gene expression. (2006) J Biol Chem 281(15):10105-10117.

Torres-Roca, J. F., et al. Prediction of radiation sensitivity using a gene expression classifier. (2005). Cancer Res 65(16):7169-7176.

Van De Vijver M. J., et al. A gene-expression signature as a predictor of survival in breast cancer. (2002) N Engl J Med 47(25):1999-2009.

Van Gelder, R. N., et al. Amplified RNA synthesized from limited quantities of heterogeneous cDNA. (1990). Proc Natl Acad Sci U S A 87:1663-1667.

Van 'T Veer, L.J., et al. Gene expression profiling predicts clinical outcome of breast cancer. (2002) Nature 415:530-536.

Wang Q., et al. DNA repair factor XPC is modified by SUMO-1 and ubiquitin following UV irradiation. (2005) Nucleic Acids Res 33(13):4023-4034.

Wang, J., et al. Loss of Tumor Suppressor p53 Decreases PTEN Expression and Enhances Signaling Pathways Leading to Activation of Activator Protein 1 and Nuclear Factor {kappa} B Induced by UV Radiation. (2005). Cancer Res 65(15):6601-6611.

Watanabe, T., et al. Prediction of sensitivity of rectal cancer cells in response to preoperative radiotherapy by DNA microarray analysis of gene expression profiles. (2006) Cancer Res 66(7):3370-3374.

Wei, G., et al. Gene expression-based chemical genomics identifies rapamycin as a modulator of MCL1 and glucocorticoid resistance. (2006). Cancer Cell 10:331-342.

Weichselbaum, R. R., et al. An interferon-related gene signature for DNA damage resistance is a predictive marker for chemotherapy and radiation for breast cancer. (2008) Proc Natl Acad Sci U S A 105(47)18490-18495.

Wendt, T. G., et al. Simultaneous radiochemotherapy versus radiotherapy alone in advanced head and neck cancer: a randomized multicenter study. (1998). J Clin Oncol 16(4):1318-1324.

West, C. M. L., et al. The independence of intrinsic radiosensitivity as a prognostic factor for patient response to radiotherapy of carcinoma of the cervix. (1997) British Journal of Cancer 76(9):1184-1190.

Kitano, H. Computational systems biology. 2002. Nature 420:206-210.

Whitney, C. W., et al. Randomized Comparison of Fluorouracil Plus Cisplatin Versus Hydroxyurea as an Adjunct to Radiation Therapy in Stage IIB-IVA Carcinoma of the Cervix With Negative Para-Aortic Lymph Nodes: A Gynecologic Oncology Group and Southwest Oncology Group Study. (1999). J Clin Oncol 17(5):1339-1348.

Wong, Y. F., et al. Gene expression pattern associated with radiotherapy sensitivity in cervical cancer. (2006) Cancer J 12:189-193.

Xu, L, et al. Merging microarray data from separate breast cancer studies provides a robust prognostic test. (2008) BMC Bioinformatics 9(125):1-14.

Zelefsky, M. J., et al. High Dose Radiation Delivered by Intensity Modulated Conformal Radiotherapy Improves the Outcome of Localized Prostate Cancer. (2001) The Journal of Urology 166:876-881.

Hood, L., et al. The impact of systems approaches on biological problems in drug discovery. (2004) Nature Biotechnology 22(10):1215-1217.

Nakajima, T., et al. Regulation of radiation-induced protein kinase C(delta) activation in radiation-induced apoptosis differs between radiosensitive and radioresistant mouse thymic lymphoma cell lines. (2006) Mutation Research 595:29-36.

Kao, G. D. et al., p34(Cdc2) kinase activity is excluded from the nucleus during the radiation-induced G(2) arrest in HeLa cells. (1999). J Biol Chem 274(49):34779-34784.

West, C. M. L. et al., Intrinsic radiosensitivity and prediction of patient response to radiotherapy for carcinoma of the cervix. (1993) Br J Cancer 68:819-823.

Hennequin et al., "Chemotherapy with cisplatinum, carboplatin and 5FU-folinic acid, followed by concomitant chemo-radiotherapy in unresectable esophageal carcinomas," Bull Cancer, 88(2):203-207 (2001).

Hennequin et al., "Impact on survival of surgery after concomitant chemoradiotherapy for locally advanced cancers of the esophagus," International Journal of Radiation Oncology, Biology, Physics, 49(3):657-664 (2001).

Herskovic et al., "Combined chemotherapy and radiotherapy compared with radiotherapy alone in patients with cancer of the esophagus," N Engl J Med, 326(24):1593-1598 (1992).

Hieronymus et al., "Gene expression signature-based chemical genomic prediction identifies a novel class of HSP90 pathway modulators," Cancer Cell, 10:321-330 (2006).

Irizarry et al., "Summaries of Affymetrix GeneChip probe level data," Nucleic Acids Res, 31(4):e15 (2003).

Janjan et al., "Improved Overall Survival Among Responders to Preoperative Chemoradiation for Locally Advanced Rectal Cancer," Am J Clin Oncol, 24(2):107-112 (2001).

Janjan et al., "Tumor downstaging and sphincter preservation with preoperative chemoradiation in locally advanced rectal cancer: the M. D. Anderson Cancer Center experience," International Journal of Radiation Oncology,Biology, Physics, 44(5):1027-1038 (1999).

Jassem, J., "Combined chemotherapy and radiation in locally advanced non-small-cell lung cancer," The Lancet Oncology, 2:335-342 (2001).

Jeong et al., "Lethality and centrality in protein networks," Nature, 411:41-42 (2001).

Jeong et al., "The large-scale organization of metabolic networks," Nature, 407:651-654 (2000).

Jeremic et al., "Hyperfractionated radiation therapy with or without concurrent low-dose daily carboplatin/etoposide for stage III non-small-cell lung cancer: a randomized study," J Clin Oncol, 14(4):1065-1070 (1996).

Jeremic et al., "Hyperfractionated Radiation Therapy With or Without Concurrent Low-Dose Daily Cisplatin in Locally Advanced Squamous Cell Carcinoma of the Head and Neck: A Prospective Randomized Trial," J Clin Oncol, 18 (7):1458-1464 (2000).

Jeremic et al., "Randomized trial of hyperfractionated radiation therapy with or without concurrent chemotherapy for stage III non-small-cell lung cancer," J Clin Oncol, 13(2):452-458 (1995).

Kaminski et al., "Effect of sequencing of androgen deprivation and radiotherapy on prostate cancer growth," International Journal of Radiation Oncology, Biology, Physics, 57(1):24-28 (2003).

Pilepich et al., "Phase III radiation therapy oncology group (RTOG) trial 86-10 of androgen deprivation adjuvant to definitive radiotherapy in locally advanced carcinoma of the prostate," International Journal of Radiation Oncology, Biology, Physics, 50(5):1243-1252 (2001).

Keys et al., "Cisplatin, Radiation, and Adjuvant Hysterectomy Compared with Radiation and Adjuvant Hysterectomy for Bulky Stage IB Cervical Carcinoma," N Engl J Med, 340:1154-1161 (1999).

Hood, L. et al., Systems Biology and New Technologies Enable Predictive and Preventative Medicine. Science 306, 640-643 (2004).
Kim et al., "The influence of Ras pathway signaling on tumor radiosensitivity," Cancer and Metastasis Reviews, 23:227-236 (2004).
Lamb, J., et al. The Connectivity Map: Using Gene-Expression Signatures to Connect Small Molecules, Genes, and Disease. Science 313, 1929-1935 (2006).
Landry, J. C., et al. Preoperative irradiation and fluorouracil chemotherapy for locally advanced rectosigmoid carcinoma: phase I-II study. Radiology 188, 423-426 (1993).
Lawton et al., "Androgen suppression plus radiation versus radiation alone for patients with stage D1/pathologic node-positive adenocarcinoma of the prostate: updated results based on national prospective randomized trial Radiation Therapy Oncology Group 85-31," J Clin Oncol, 23(4):800-807 (2005).
Li et al., "AKT-independent protection of prostate cancer cells from apoptosis mediated through complex formation between the androgen receptor and FKHR," Mol Cell Biol, 23(1):104-118 (2003).
Li et al., "Ionizing radiation and short wavelength UV activate NF-kappa B through two distinct mechanisms," PNAS, 95:13012-13017 (1998).
Lindsay et al., "The genetic basis of tissue responses to ionizing radiation," Br J Radiol, 80:S2-6 (2007).
Liu et al., "NF-[kappa]B Is Required for UV-Induced JNK Activation via Induction of PKCδ," Molecular Cell, 21:467-480 (2006).
Lorvidhaya et al., "Concurrent mitomycin C, 5-fluorouracil, and radiotherapy in the treatment of locally advanced carcinoma of the cervix: a randomized trial," International Journal of Radiation Oncology,Biology,Physics, 55 (5):1226-1232 (2003).
Ma et al., "Combined-Modality Treatment of Solid Tumors Using Radiotherapy and Molecular Targeted Agents," J Clin Oncol, 21(14):2760-2776 (2003).
Malaise et al., "Distribution of radiation sensitivities for human tumor cells of specific histological types: comparison of in vitro to in vivo data," International Journal of Radiation Oncology, Biology, Physics, 12:617-624 (1986).
Mao et al., "SUMO-1 conjugation to topoisomerase I: A possible repair response to topoisomerase-mediated DNA damage," Proc Natl Acad Sci U S, 97(8):4046-4051 (2000).
Marples et al., "Low-dose hyper-radiosensitivity: past, present, and future," Int J Radiat Oncol Biol Phys, 70 (5):1310-1318 (2008).
Massague, J., "Sorting out breast-cancer gene signatures," N. Engl. J. Med., 356(3): 294-297 (2007).
Mialon et al., "DNA topoisomerase I is a cofactor for c-Jun in the regulation of epidermal growth factor receptor expression and cancer cell proliferation," Mol. Cell Biol., 25(12):5040-5051 (2005).
Milas et al., "Chemoradiotherapy: Emerging treatment improvement strategies" Head & Neck, 25:152-167 (2003).
Minsky et al., "Enhancement of radiation-induced downstaging of rectal cancer by fluorouracil and high-dose leucovorin chemotherapy," J. Clin. Oncol., 10(1):79-84 (1992).
Moeller et al., "Hypoxia and radiotherapy: opportunities for improved outcomes in cancer treatment," Cancer Metastasis Rev., 26:241-248 (2007).
Mohiuddin et al., "Preoperative chemoradiation in fixed distal rectal cancer: dose time factors for pathological complete response," International Journal of Radiation Oncology, Biology, Physics, 46(4):883-888 (2000).
Mohiuddin et al., "Prognostic significance of postchemoradiation stage following preoperative chemotherapy and radiation for advanced/recurrent rectal cancers," Int. J. Radiat. Oncol. Biol. Phys., 48(4):1075-1080 (2000).
Morris et al., "Pelvic Radiation with Concurrent Chemotherapy Compared with Pelvic and Para-Aortic Radiation for High-Risk Cervical Cancer," N. Engl. J. Med., 340(15):1137-1143 (1999).
Movsas et al., "Hypoxic prostate/muscle pO2 ratio predicts for biochemical failure in patients with prostate cancer: preliminary findings," Urology, 60:634-639 (2002).
Nahta et al., "Mechanisms of disease: understanding resistance to HER2-targeted therapy in human breast cancer," Nat. Clin. Pract. Oncol., 3(5):269-280 (2006).

Nakajima et al., "Involvement of protein kinase C-related anti-apoptosis signaling in radiation-induced apoptosis in murine thymic lymphoma(3SBH5) cells," Radiat. Res., 161:528-534 (2004).
Nakajima et al., "Regulation of radiation-inducted protein kinase Cdelta activation in radiation-induced apoptosis differs between radiosensitive and radioresistant mouse thymic lymphoma cell lines," Mutat. Res., 595:29-36 (2006).
Narlikar et al., "Cooperation between Complexes that Regulate Chromatin Structure and Transcription," Cell, 108:475-487 (2002).
Pamment et al., "Regulation of the IRF-1 tumour modifier during the response to genotoxic stress involves an ATM-dependent signalling pathway," Oncogene, 21:7776-7785 (2002).
Peeters et al., "Acute and late complications after radiotherapy for prostate cancer: results of a multicenter randomized trial comparing 68 Gy to 78 Gy," Int. J. Radiat. Oncol. Biol. Phys., 61(4):1019-1034, (2005).
Perez, C. et al., "Principles and Management of Radiation Therapy," Philadelphia-New York, Lippincott-Raven (1998).
Peters et al., "Concurrent Chemotherapy and Pelvic Radiation Therapy Compared With Pelvic Radiation Therapy Alone as Adjuvant Therapy After Radical Surgery in High-Risk Early-Stage Cancer of the Cervix," J. Clin. Oncol., 18 (8):1606-1613 (2000).
Peters et al., "Predictive assays of tumor radiocurability," Am. J. Clin. Oncol., 11(3):275-287 (1988).
Peters, L. J., "The ESTRO Regaud lecture. Inhernet radiosensitivity of tumor and normal tissue cells as a predictor of human tumor response," Radiother. Oncol., 17:177-190 (1990).
Albert et al., "Error and attack tolerance of complex networks," Nature, 406:378-382 (2000).
Algan et al., "Management of adenocarcinoma of the esophagus with chemoradiation alone or chemoradiation followed by esophagectomy: results of sequential nonrandomized phase II studies," International journal of radiation oncology, biology, physics, 32(3):753-761 (1995).
Ailizadeh et al., "Distinct types of diffuse large B-cell lymphoma identified by gene expression profiling," Nature, 403:503-511 (2000).
Al-Sarraf et al., "Chemoradiotherapy versus radiotherapy in patients with advanced nasopharyngeal cancer: phase III randomized Intergroup study 0099," J Clin Oncol, 16(4):1310-1317 (1998).
Al-Sarraf et al., "Progress report of combined chemoradiotherapy versus radiotherapy alone in patients with esophageal cancer: an intergroup study," J Clin Oncol, 15(1):277-284 (1997).
Beer et al., "Gene-expression profiles predict survival of patients with lung adenocarcinoma," Nat Med, 8(8):816-824 (2002).
Begg et al., "The value of pretreatment cell kinetic parameters as predictors for radiotherapy outcome in head and neck cancer: a multicenter analysis," Radiother Oncol, 50:13-23 (1999).
Bild et al., "Oncogenic pathway signatures in human cancers as a guide to targeted therapies," Nature, 439:353-357 (2006).
Bjork-Eriksson et al., "Tumor radiosensitivity (SF2) is a prognostic factor for local control in head and neck cancers," Int J Radiat Oncol Biol Phys, 46(1):13-19 (2000).
Bolla et al., "Improved Survival in Patients with Locally Advanced Prostate Cancer Treated with Radiotherapy and Goserelin," N Engl J Med, 337(5):295-300 (1997).
Bolla et al., "Long-term results with immediate androgen suppression and external irradiation in patients with locally advanced prostate cancer (an EORTC study): a phase III randomised trial," The Lancet 360:103-108 (2002).
Bosset et al., "Chemotherapy with Preoperative Radiotherapy in Rectal Cancer," N Engl J Med, 355(11):1114-1123 (2006).
Bourhis et al., "Potential doubling time and clinical outcome in head and neck squamous cell carcinoma treated with 70 GY in 7 weeks," Int J Radiat Oncol Biol Phys, 35(3):471-476 (1996).
Brizel et al., "Hyperfractionated Irradiation with or without Concurrent Chemotherapy for Locally Advanced Head and Neck Cancer," N Engl J Med, 338:1798-1804 (1998).
Browman et al., "Choosing a concomitant chemotherapy and radiotherapy regimen for squamous cell head and neck cancer: A systematic review of the published literature with subgroup analysis," Head & Neck, 23:579-589 (2001).

Bucci et al., "Advances in Radiation Therapy: Conventional to 3D, to IMRT, to 4D, and Beyond," CA Cancer J Clin, 55:117-134 (2005).

Buffa et al., "Incorporating biologic measurements (SF(2), CFE) into a tumor control probability model increases their prognostic significance: a study in cervical carcinoma treated with radiation therapy," Int J Radiat Oncol Biol Phys, 50 (5):1113-1122 (2001).

Capirci et al., "Prognostic Value of Pathologic Complete Response After Neoadjuvant Therapy in Locally Advanced Rectal Cancer: Long-term Analysis of 566 ypCR Patients," International Journal of Radiation Oncology Biology Physics, 72(1):99-107 (2008).

Cerna et al., "Histone deacetylation as a target for radiosensitization," Curr Top Dev Biol, 73:173-204 (2006).

Chang et al., "GATHER: a systems approach to interpreting genomic signatures," Bioinformatics, 22(23):2926-2933 (2006).

Chen et al., "Downstaging of advanced rectal cancer following combined preoperative chemotherapy and high dose radiation," International Journal of Radiation Oncology, Biology, Physics, 30(1):169-175 (1994).

Chinnaiyan et al., "Modulation of radiation response by histone deacetylase inhibition," Int J Radiat Oncol Biol Phys, 62(1):223-229 (2005).

Chirieac et al., "Posttherapy pathologic stage predicts survival in patients with esophageal carcinoma receiving preoperative chemoradiation," Cancer, 103:1347-1355 (2005).

Cho et al., "Topoisomerase I inhibitors in the combined-modality therapy of lung cancer," Oncology, 18:29-39 (2004).

Chung et al., "Molecular classification of head and neck squamous cell carcinomas using patterns of gene expression," Cancer Cell, 5:489-500 (2004).

Corvo et al., "In vivo cell kinetics in head and neck squamous cell carcinomas predicts local control and helps guide radiotherapy regimen," J Clin Oncol, 13(8):1843-1850 (1995).

Cox et al., "The dark side of Ras: regulation of apoptosis," Oncogene, 22:8999-9006 (2003).

Cuddihy et al., "The p53 protein family and radiation sensitivity: Yes or no?" Cancer Metastasis Rev, 23:237-257 (2004).

D'Amico et al., "6-Month Androgen Suppression Plus Radiation Therapy vs Radiation Therapy Alone for Patients With Clinically Localized Prostate Cancer: A Randomized Controlled Trial," JAMA, 292(7):821-827 (2004).

Dalton et al., "Cancer biomarkers—an invitation to the table," Science 312:1165-1168 (2006).

Deng et al., "Caenorhabditis Elegans ABL-1 Antogonizes p53-Mediated Germline Apoptosis After Ionizing Irradiation," Nature Genetics, 36(8):906-912 (2004).

Denis et al., "Final Results of the 94-01 French Head and Neck Oncology and Radiotherapy Group Randomized Trial Comparing Radiotherapy Alone With Concomitant Radiochemotherapy in Advanced-Stage Oropharynx Carcinoma," J Clin Oncol, 22(1):69-76 (2004).

Deschavanne et al., "A review of human cell radiosensitivity in vitro," Int J Radiat Oncol Biol Phys, 34(1):251-266 (1996).

Dobbin et al., "Interlaboratory comparability study of cancer gene expression analysis using oligonucleotide microarrays," Clin Cancer Res, 11:565-572 (2005).

Eifel et al., "Pelvic Irradiation With Concurrent Chemotherapy Versus Pelvic and Para-Aortic Irradiation for High-Risk Cervical Cancer: An Update of Radiation Therapy Oncology Group Trial (RTOG) 90-01," J Clin Oncol, 22(5):872-880 (2004).

El-Deiry, W. S., "The role of p53 in chemosensitivity and radiosensitivity," Oncogene, 22:7486-7495 (2003).

Eschrich et al., "Molecular staging for survival prediction of colorectal cancer patients," J Clin Oncol, 23 (15):3526-3535 (2005).

Eschwege et al., "Predictive assays of radiation response in patients with head and neck squamous cell carcinoma: a review of the Institute Gustave Roussy experience," Int J Radiat Oncol Biol Phys, 39(4):849-853 (1997).

Fertil et al., "Inherent cellular radiosensitivity as a basic concept for human tumor radiotherapy," Int J Radiat Oncol Biol Phys, 7(5):621-629 (1981).

Fertil et al., "Intrinsic radiosensitivity of human cell lines is correlated with radioresponsiveness of human tumors: analysis of 101 published survival curves," International Journal of Radiation Oncology, Biology, Physics, 11:1699-1707 (1985).

Fiorica et al., "Preoperative chemoradiotherapy for oesophageal cancer: a systematic review and meta-analysis," Gut, 53(7):925-930 (2004).

Fryknas et al., "STAT1 signaling is associated with acquired crossresistance to doxorubicin and radiation in myeloma cell lines," International Journal of Cancer, 120:189-195 (2006).

Furuse et al., "Phase III Study of Concurrent Versus Sequential Thoracic Radiotherapy in Combination With Mitomycin, Vindesine, and Cisplatin in Unresectable Stage III Non-Small-Cell Lung Cancer," J Clin Oncol, 17 (9):2692-2699 (1999).

Fyles et al., "Tumor hypoxia has independent predictor impact only in patients with node-negative cervix cancer," J Clin Oncol, 20(3):680-687 (2002).

Gavioli et al., "Incidence and Clinical Impact of Sterilized Disease and Minimal Residual Disease After Preoperative Radiochemotherapy for Rectal Cancer," Dis Colon Rectum, 48:1851-1857 (2005).

Giles et al., "Optimizing outcomes for patients with advanced disease in chronic myelogenous leukemia," Semin Oncol, 35:S1-17 (2008).

Gudkov et al., "The Role of p53 in Determining Sensitivity to Radiotherapy," Nature Reviews Cancer, 3:117-129 (2003).

Hallahan et al., "Prolonged c-jun expression in irradiated ataxia telangiectasia fibroblasts," International Journal of Radiation Oncology, Biology, Physics, 36(2):355-360 (1996).

Hallahan et al., "Radiation signaling mediated by Jun activation following dissociation from a cell type-specific repressor," J Biol Chem, 268(7):4903-4907 (1993).

Hanks et al., "Phase III Trial of Long-Term Adjuvant Androgen Deprivation After Neoadjuvant Hormonal Cytoreduction and Radiotherapy in Locally Advanced Carcinoma of the Prostate: The Radiation Therapy Oncology Group Protocol 92-02," J Clin Oncol, 21(21):3972-3978 (2003).

* cited by examiner

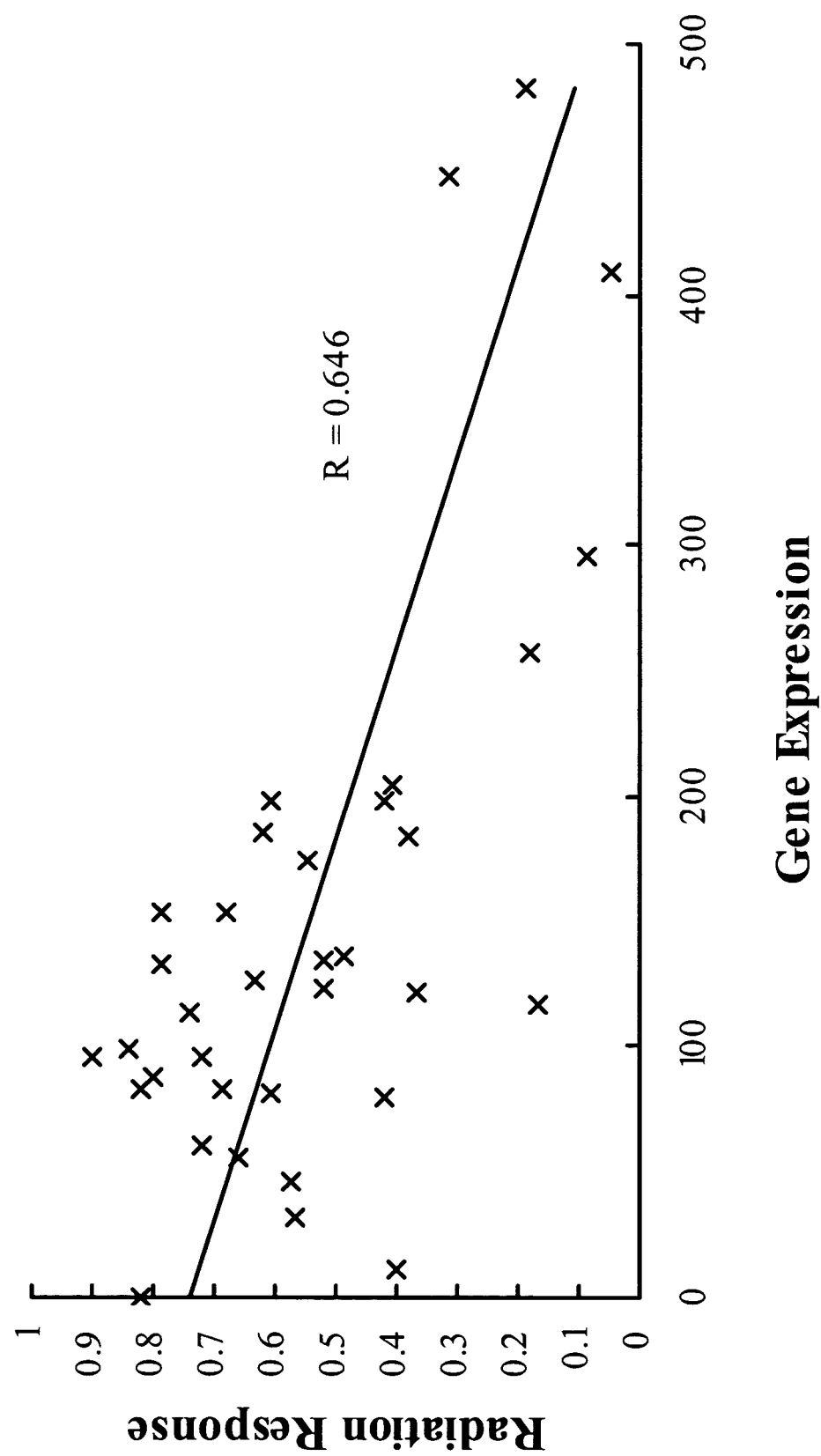
Fig. 2B G Protein Signalling Regulator 19

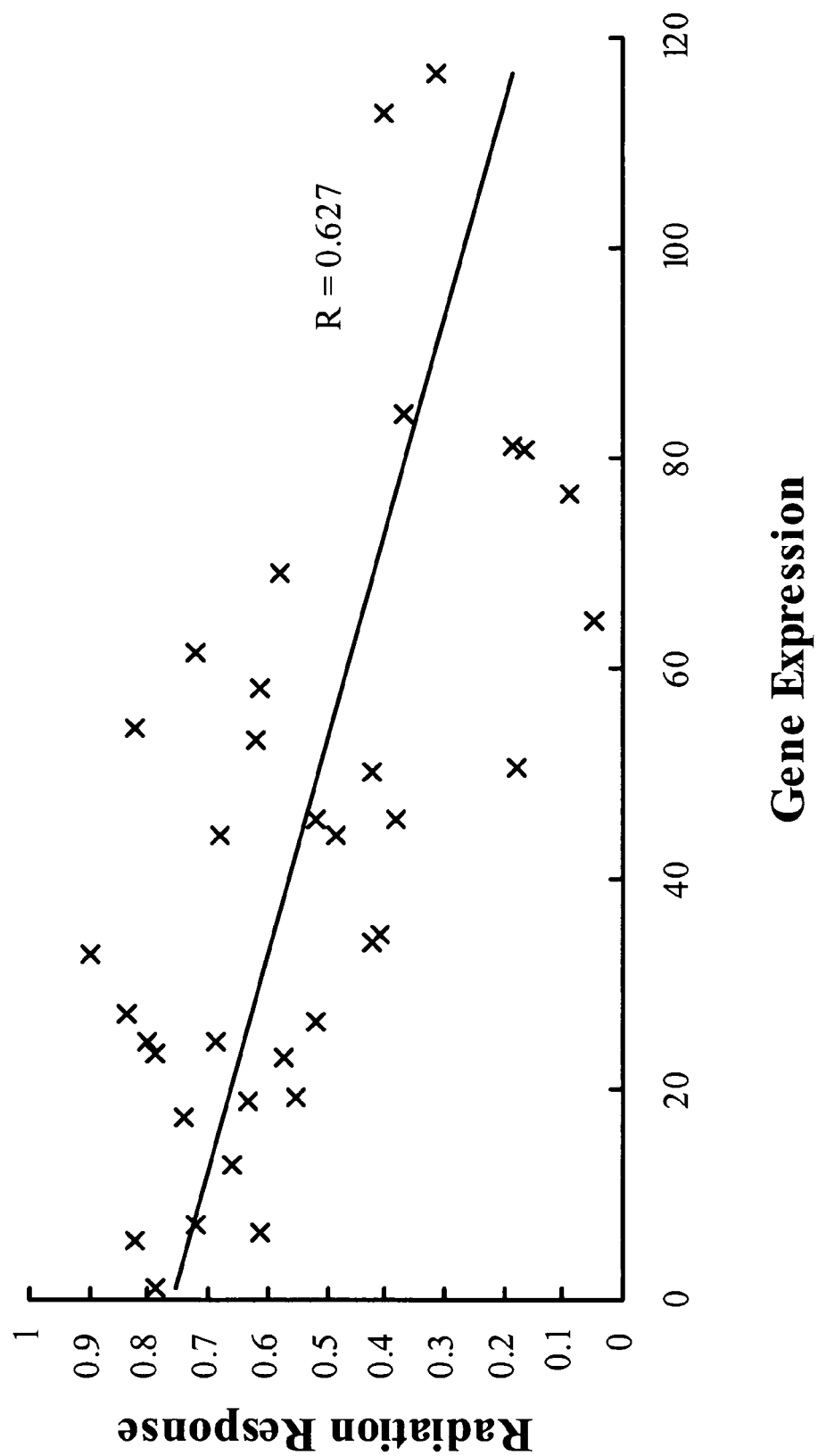

Hs-578T Clonogenic Assay

Figure 6

| Cell Line | Classification | Predicted SF 2 | Measured SF 2 | Cutoff for Correct Classification | Difference Predicted and Measured SF2 |
|---|---|---|---|---|---|
| BREAST_BT549 | Correct | 0.58 | 0.63 | 0.53 | -0.056 |
| BREAST_HS578T | Correct | 0.79 | 0.79 | 0.69 | -0.004 |
| BREAST_MDAMB231 | Correct | 0.53 | 0.82 | 0.44 | -0.288 |
| BREAST_T47D | Correct | 0.62 | 0.52 | 0.62 | 0.095 |
| CNS_U251 | Correct | 0.67 | 0.57 | 0.71 | 0.097 |
| COLON_COLO205 | Correct | 0.59 | 0.69 | 0.59 | -0.104 |
| COLON_HCT116 | Correct | 0.41 | 0.38 | 0.48 | 0.025 |
| COLON_HCT15 | Correct | 0.46 | 0.4 | 0.5 | 0.059 |
| COLON_HT29 | Correct | 0.64 | 0.79 | 0.56 | -0.148 |
| MELAN_M14 | Correct | 0.37 | 0.42 | 0.32 | -0.046 |
| MELAN_MALME3M | Correct | 0.72 | 0.8 | 0.7 | -0.079 |
| MELAN_SKMEL2 | Correct | 0.74 | 0.66 | 0.76 | 0.08 |
| MELAN_SKMEL28 | Correct | 0.65 | 0.74 | 0.64 | -0.089 |
| NSCLC_A549ATCC | Correct | 0.55 | 0.61 | 0.43 | -0.055 |
| NSCLC_H460 | Correct | 0.74 | 0.84 | 0.74 | -0.097 |
| OVAR_OVCAR3 | Correct | 0.58 | 0.55 | 0.65 | 0.033 |
| OVAR_OVCAR5 | Correct | 0.52 | 0.41 | 0.65 | 0.116 |
| PROSTATE_DU145 | Correct | 0.62 | 0.52 | 0.63 | 0.098 |
| PROSTATE_PC3 | Correct | 0.6 | 0.48 | 0.61 | 0.115 |
| RENAL_A498 | Correct | 0.67 | 0.61 | 0.71 | 0.056 |
| RENAL_ACHN | Correct | 0.69 | 0.72 | 0.62 | -0.031 |
| RENAL_CAKI1 | Correct | 0.38 | 0.37 | 0.47 | 0.009 |

Figure 7

| Cell Line | Classification | Predicted SF2 | Measured SF2 | Cutoff for Correct Classification | Difference Predicted and Measured SF2 |
|---|---|---|---|---|---|
| BREAST_MCF7 | Incorrect | 0.37 | 0.58 | 0.44 | -0.21 |
| BREAST_MDAMB435 | Incorrect | 0.5 | 0.18 | 0.28 | 0.32 |
| CNS_SF539 | Incorrect | 0.68 | 0.82 | 0.72 | -0.14 |
| COLON_KM12 | Incorrect | 0.56 | 0.42 | 0.52 | 0.14 |
| COLON_SW620 | Incorrect | 0.46 | 0.62 | 0.52 | -0.16 |
| LEUK_CCRFCEM | Incorrect | -0.13 | 0.19 | 0.09 | -0.32 |
| LEUK_HL60 | Incorrect | -0.01 | 0.32 | 0.17 | -0.33 |
| LEUK_MOLT4 | Incorrect | 0.46 | 0.05 | 0.15 | 0.41 |
| MELAN_LOXIMVI | Incorrect | 0.44 | 0.68 | 0.58 | -0.24 |
| MELAN_SKMEL5 | Incorrect | 0.51 | 0.72 | 0.62 | -0.21 |
| NSCLC_HOP62 | Incorrect | 0.52 | 0.16 | 0.26 | 0.35 |
| NSCLC_NCIH23 | Incorrect | 0.7 | 0.09 | 0.19 | 0.61 |
| OVAR_SKOV3 | Incorrect | 0.6 | 0.9 | 0.8 | -0.3 |

Figure 8

| Gene | No. of times selected by SAM |
|---|---|
| Ribose 5 phosphate Isomerase A | 35/35 |
| Retinoblastoma binding protein 4 | 34/35 |
| G-protein signalling regulator 19 | 34/35 |
| Affy ID HG4236-HT4506 | 33/35 |
| TBP-associated factor 5 | 12/35 |
| DNA topoisomerase | 9/35 |
| Nuclear autoantigenic sperm protein | 2/35 |
| Splicing factor 1 | 1/35 |
| Lamin B-1 | 1/35 |

IDENTIFICATION OF NOVEL TARGETS FOR RADIO SENSITIZATION USING A GENOMIC-BASED RADIATION SENSITIVITY CLASSIFIER

CROSS REFERNCE TO RELATED APPLICATION

This application claims priority from U.S. provisional application Ser. No. 60/481,604, entitled: "Radiation Sensitivity Classifier", filed Nov. 5, 2003.

STATEMENT OF GOVERNMENT INTEREST

The subject invention was made with government support under a research project supported by National Institute of Health Grant No. CA108926. The federal government may have certain rights in this invention.

BACKGROUND OF THE INVENTION

Radiation Therapy has played a major role in cancer therapeutics since its discovery more than one hundred years ago. It is estimated that in the United States and Europe more than one million individuals receive radiation therapy every year as part of their cancer treatment. Radiation therapy can be curative, particularly in prostate cancer, head and neck cancer and cervical cancer where cure rates with definitive radiation therapy are comparable with those achieved with radical surgery. It also plays an important role in multi-modality organ conservation protocols as in breast cancer, rectal cancer, soft tissue sarcoma and laryngeal cancer where cure rates have been equaled to those achieved with radical surgery with the advantage of organ function preservation.

In the last decade a significant improvement in the cure rates and overall survival of cervical, head and neck and lung cancer has been achieved by delivering concurrent radiotherapy and chemotherapy (radiochemotherapy). Phase III prospective randomized trials have shown concurrent radiochemotherapy improves overall survival over standard radiotherapy in cervical, head and neck, esophageal and lung cancer. In general the beneficial effect of concurrent radiochemotherapy has been ascribed to the radiosensitization effect induced by chemotherapy, which makes both normal and malignant cells more sensitive to radiation-induced damage. Interestingly, most drugs used in these trials have not been developed as "radiosensitizers" but have been discovered to radiosensitize after they have been tested in the clinic as cancer toxic agents. Therefore the development of targeted radiosensitizing drugs is an attractive area of research with significant clinical potential.

A major hurdle to the development of better radiosensitizing drugs has been the limited number of known potential targets. In the last decade significant advances in our molecular understanding of radiation response has led to the development of several promising targeted radiosensitizers, some of which are currently undergoing clinical evaluation. The radiation signaling pathways addressed by these radiosensitizers include: Ras/PI3K/Akt which may be activated directly by tyrosine kinases or receptor-activated Ras, DNA repair (DNA-PK, PARP-1), cyclooxygenase-2 (COX-2), toposimorease-I, Epidermal Growth Factor (EGF) and others. However it is very likely that the number of unknown molecular pathways/targets involved in radiation response outnumber the number of known targets. With the advent of the functional genomics era, it is hoped that technologies may be developed that may allow us to identify potential targets using a genomic approach.

SUMMARY OF INVENTION

The unexpected observations below provide the basis for this invention, which is directed to a method of identifying novel targets for radiosensitization using a genomic-based radiation sensitivity classifier. Additionally, the present invention includes a method of increasing the sensitivity of human tumor cells to irradiation. Such a method include a novel method of treating a human tumor cell by introducing a nucleic acid encoding a polypeptide which increases the expression of the radiosensitization targets discussed infra, and thus increasing the radiation sensitivity of tumor cells. The methods may be practiced in vitro or in vivo.

Another embodiment of the present invention includes a method of generating a radiation classifier for predicting cellular radiation sensitivity comprising the steps of establishing the radiation sensitivity of at least one cell line, establishing the genomic expression of the at least one cell line, and identifying at least one gene of interest, expressed by the at least one cell line, predictive of a radiation response. The at least one cell line is established by the survival fraction of the at least one cell line after exposure to about 2 Gy of radiation, which can be established from in lab experimentation or a microarray. The gene of interest is identified by measuring the correlation between the expression of the gene of interest and the radiation sensitivity of the cell line expressing the gene. The correlation between the expression of the gene of interest and the radiation sensitivity of the cell line expressing the gene can be measured using any sufficient statistical method, such as Significant Analysis of Microarrays.

Another embodiment includes a method of predicting a clinical response to radiation therapy of a subject in need thereof comprising the steps of obtaining a sample of target cells from the subject, identifying a radiation classifier expressed by the sample, and determining an expression value of the radiation classifier by the target cells whereby a high expression value correlates with a radiosensitive phenotype thereby predicting the clinical response to treatment with radiation therapy. In one embodiment the sample of target cells comprises cancer cells. The expression level of the radiation classifier is determined using a quantitative real-time polymerase chain reaction. The radiation classifier can be a gene whose expression values correlate with radiation sensitivity thereby conferring radiation sensitivity to the cell, as determined from a baseline genomic expression for the target cell (possibly determined by the use of microarrays). In possible embodiments the gene of interest is selected from the group consisting of retinoblastoma binding protein 4 (RbAp48), G-protein signaling regulator 19 (RGS19), and ribose-5-phosphate isomerase A (R5PIA).

Yet another embodiment includes a method of increasing the viability of a target cell expressing a gene of interest, during radiation therapy, in a subject comprising the step of contacting the target cell containing the gene of interest with an effective amount of an oligonucleotide targeted to a nucleic acid encoding the gene of interest, wherein said oligonucleotide is capable of inhibiting expression of the gene of interest, thereby conferring a radiation resistant phenotype to the target cell. The gene of interest is selected from a baseline genomic expression for the target cell (possibly using microarrays). In possible embodiments the gene of interest is selected from the group consisting of retinoblastoma binding protein 4 (RbAp48), G-protein signaling regulator 19 (RGS 19), and ribose-5-phosphate isomerase A (R5PIA).

In yet another embodiment a method of decreasing the viability of a target cell, expressing a gene of interest, in a subject comprising the steps of contacting the target cell containing the gene of interest with an effective amount of an oligonucleotide targeted to a nucleic acid encoding the gene of interest, wherein said oligonucleotide is capable of increasing expression of the gene of interest, thereby conferring a radiation sensitive phenotype to the target cell and contacting the target cell with a therapeutically effective amount of radiation is provided. The gene of interest is selected from a baseline genomic expression for the target cell (possibly using microarrays). In possible embodiments the gene of interest is selected from the group consisting of retinoblastoma binding protein 4 (RbAp48), G-protein signaling regulator 19 (RGS19), and ribose-5-phosphate isomerase A (R5PIA).

BRIEF DESCRIPTION OF THE DRAWINGS

For a fuller understanding of the nature and objects of the invention, reference should be made to the following detailed description, taken in connection with the accompanying drawings, in which:

FIGS. 2A through 2C are graphs showing a linear correlation between the expression values of each of the "predictive" genes and radiation sensitivity.

FIG. 6 is a table showing the results of the classifier.

FIG. 7 is a table showing the results of the classifier.

FIG. 8 is a table showing the list of genes that were selected by SAM analysis to be predictive of radiation response

DETAILED DESCRIPTION OF THE PREFERRED EMBODIMENT

Figure 1:
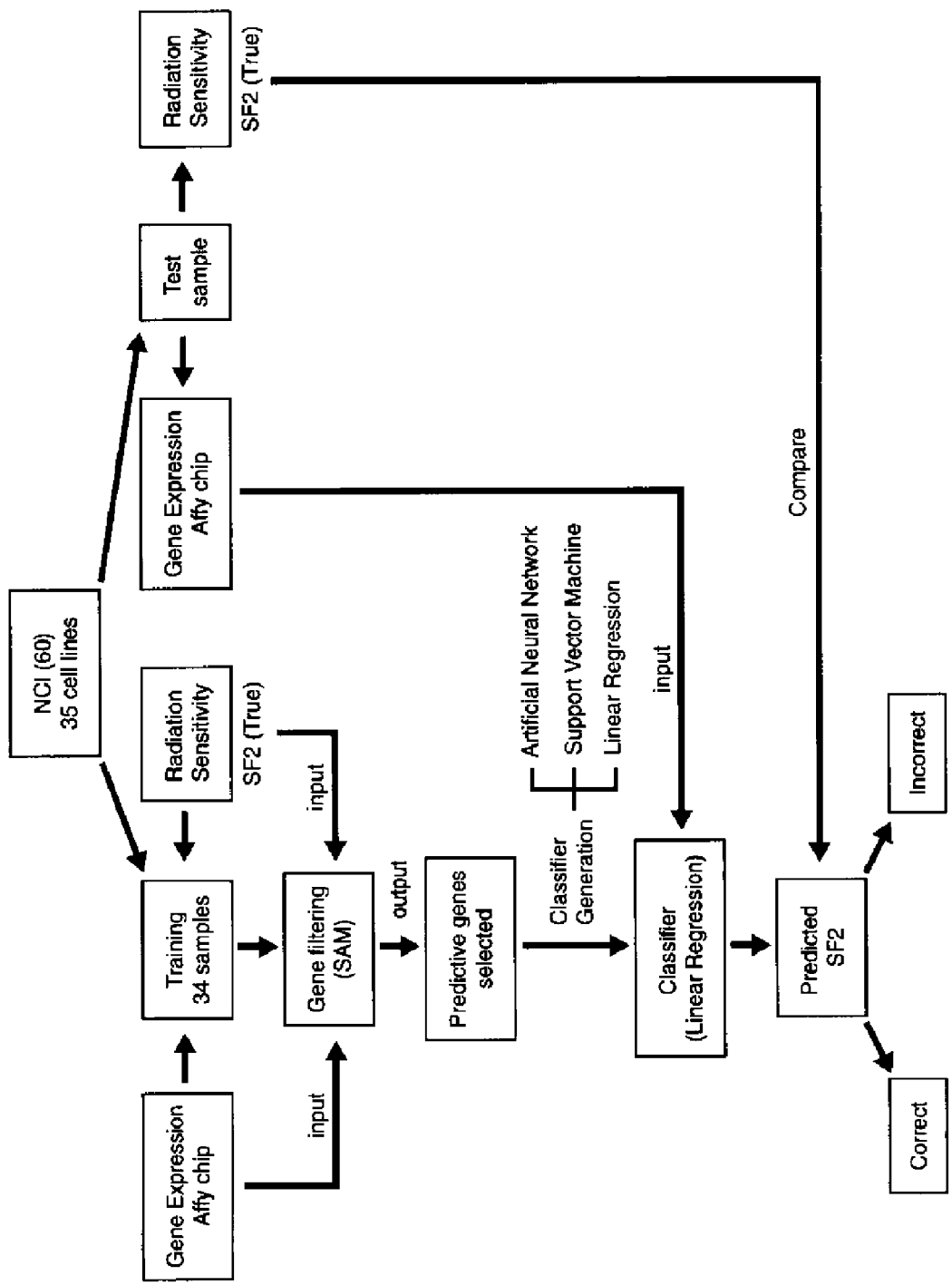
FIG. 1 is a block diagram showing the general scheme of the classifier.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The association between the target gene expression and radiation resistance was discovered during a search for genes that are more highly expressed in radiation sensitive cell lines than in relatively radiation resistant cell lines.

The invention is based on a genome-wide approach to the identification of radiation response molecular targets that may be exploited therapeutically by developing radiosensitizing drugs that affect the target/targets identified by the classifier. The targets identified by the invention can also be used for developing prognostic tests that predict the likelihood of response to radiation therapy as well as the development of diagnostic and predictive imaging technologies. The inventors reasoned that the development of a genomic-based radiation sensitivity classifier could potentially lead to the identification of novel genes or targets involved in radiation sensitivity/radiation response, by correlating radiation sensitivity and gene expression profiles. The clinical potential of such an analytical approach is significant, as it allows a genome-wide high throughput analysis of potential targets involved in radiation sensitivity/radiation response. The inventors hypothesized that a radiation classifier or predictor can be developed based on cellular gene expression profiles derived from DNA microarrays. This hypothesis is based on the fact that the three main mechanisms, which have been shown to play a role in clinical failure after RT (hypoxia, intrinsic radiosensitivity and cellular proliferation) are known to induce genetic change.

The studies described below in Example I demonstrate that the target gene is expressed at a higher level in certain radiation sensitive cells than in relatively radiation resistant cells. The studies in Example II establish that the level of expression of the target gene is an accurate indicator of a cell's sensitivity or resistance to radiation therapy. Example III demonstrates that Quantitative RT-PCR validated the studies indicating the accuracy of the gene expression values determined by the microarrays. The studies described in Example 4 provide evidence that increasing the expression of the target gene renders cells more sensitive to radiation.

The term "gene of interest" or "target gene" refers to a nucleic acid sequence which can be of any origin and isolated from a genomic DNA, a cDNA, or any DNA encoding a RNA, such as a genomic RNA, a mRNA, an anti-sense RNA, a ribosomal RNA, a ribozyme or a transfer RNA. The gene of interest can also be an oligonucleotide (i.e., a nucleic acid having a short size of less than 100 bp). It can be engineered from genomic DNA to remove all or part of one or more intronic sequences (i.e., minigene).

In a one embodiment, the gene of interest in use in the present invention, encodes a target gene product, such as a protein, of therapeutic interest. A gene product of therapeutic interest, or target gene protein, is one which has a therapeutic or protective activity when administered appropriately to a patient, especially a patient suffering from a disease or illness condition or who should be protected against this disease or condition. Such a therapeutic or protective activity can be correlated to a beneficial effect on the course of a symptom of said disease or said condition. It is within the reach of the man skilled in the art to select a gene encoding an appropriate gene product of therapeutic interest, depending on the disease or condition to be treated. In a general manner, his choice may be based on the results previously obtained, so that he can reasonably expect, without undue experimentation, i.e., other than practicing the invention as claimed, to obtain such therapeutic properties.

In the context of the invention, the gene of interest can be homologous or heterologous to the host cell into which it is introduced. Advantageously, it encodes a polypeptide, a ribozyme or an anti-sense RNA. The term "polypeptide" is to be understood as any translational product of a polynucleotide whatever its size is, and includes polypeptides having as few as 7 residues (peptides), but more typically proteins. In addition, it may be from any origin (prokaryotes, lower or higher eukaryotes, plant, virus etc). It may be a native polypeptide, a variant, a chimeric polypeptide having no counterpart in nature or fragments thereof. Advantageously, the gene of interest in use in the present invention encodes at least one polypeptide that can compensate for one or more defective or deficient cellular proteins in an animal or a human organism, or that acts through toxic effects to limit or remove harmful cells from the body. A suitable polypeptide may also be immunity conferring and acts as an antigen to provoke a humoral or a cellular response, or both.

Representative examples of polypeptides encoded by the gene of interest include without limitation polypeptides selected from the group consisting of polypeptides involved in the cellular cycle, particularly the radiation signaling pathways, such as retinoblastoma binding protein 4 (RbAp48), G-protein signaling regulator 19 (RGS19), and ribose-5-phosphate isomerase A (R5PIA).

The inventive method includes determining the sensitivity of a cell expressing one or more nucleic acids, operably linked to a gene of interest, to radiation therapy. The phrases "nucleic acid" or "nucleic acid sequence" as used herein refers to an oligonucleotide, nucleotide, polynucleotide, or to a fragment of any of these, to DNA or RNA of genomic or synthetic origin which may be single-stranded or double-stranded and may represent a sense or antisense strand, peptide nucleic acid (PNA), or to any DNA-like or RNA-like material, natural or synthetic in origin. As will be understood by those of skill in the art, when the nucleic acid is RNA, the deoxynucleotides A, G, C, and T are replaced by ribonucleotides A, G, C, and U, respectively.

In general, the target nucleic acid is DNA. However, invention methods may employ, for example, samples that contain DNA, or DNA and RNA, including messenger RNA, wherein DNA or RNA may be single stranded or double stranded, or a DNA-RNA hybrid may be included in the sample. A mixture of nucleic acids may also be employed. The specific nucleic acid sequence to be detected may be a fraction of a larger molecule or can be present initially as a discrete molecule, so that the specific sequence constitutes the entire nucleic acid. It is not necessary that the sequence to be studied be present initially in a pure form; the nucleic acid may be a minor fraction of a complex mixture, such as contained in whole human DNA. The nucleic acid-containing sample used for determination of the sensitivity of the target cells to radiation therapy may be extracted by a variety of techniques such as that described by Sambrook, et al. (Molecular Cloning: A Laboratory Manual, Cold Spring Harbor, N.Y., 1989; incorporated in its entirety herein by reference).

Cells expressing the target nucleic acid isolated from a subject can be obtained in a biological specimen from the subject. The cells, or nucleic acid, can be isolated from tumor tissue, brain tissue, cerebrospinal fluid, blood, plasma, serum, lymph, lymph nodes, spleen, liver, bone marrow, or any other biological specimen. Tumor tissue, blood, plasma, serum, lymph, brain tissue, cerebrospinal fluid and bone marrow are obtained by various medical procedures known to those of skill in the art.

A cell proliferative disorder as described herein may be a neoplasm. Such neoplasms are either benign or malignant. The term "neoplasm" refers to a new, abnormal growth of cells or a growth of abnormal cells that reproduce faster than normal. A neoplasm creates an unstructured mass (a tumor) which can be either benign or malignant. The term "benign" refers to a tumor that is noncancerous, e.g. its cells do not invade surrounding tissues or metastasize to distant sites. The term "malignant" refers to a tumor that is metastastic, invades contiguous tissue or no longer under normal cellular growth control.

As used herein, "a clinical response" is the response of the tumor to treatment with radiation therapy. Criteria for determining a response to therapy are widely accepted and enable comparisons of the efficacy alternative treatments (see Slapak and Kufe, Principles of Cancer Therapy, in Harrisons's Principles of Internal Medicine, 13$^{th}$ edition, eds. Isselbacher et al., McGraw-Hill, Inc. 1994). A complete response (or complete remission) is the disappearance of all detectable malignant disease. A partial response is an approximately 50 percent decrease in the product of the greatest perpendicular diameters of one or more lesions. There can be no increase in size of any lesion or the appearance of new lesions. Progressive disease means at least an approximately 25 percent increase in the product of the greatest perpendicular diameter of one lesion or the appearance of new lesions. The response to treatment is evaluated after the subjects had completed therapy.

Expression Vectors and Host Cells

Vectors, preferably expression vectors, containing a nucleic acid encoding the target gene (or a portion thereof) are useful in the methods of the invention. A vector is a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operatively linked. In general, expression vectors of utility in recombinant DNA techniques are often in the form of plasmids (vectors, e.g., viral vectors, replication defective retroviruses, adenoviruses and adeno-associated viruses).

Useful recombinant expression vectors comprise the target gene nucleic acid in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. An expression vector can be introduced into host cells to thereby produce proteins or peptides, including fusion proteins or peptides, encoded by nucleic acids as described herein (e.g., the target gene proteins, mutant forms of the target gene, fusion proteins, etc.).

The recombinant expression vectors of the invention can be designed for expression of the target gene in prokaryotic or eukaryotic cells, e.g., bacterial cells such as E. coli, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

The target gene nucleic acid can be expressed in mammalian cells using a mammalian expression vector. Examples of mammalian expression vectors include pCDM8 (Seed (1987) Nature 329:840) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al. (supra).

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natil. Acad. Sci. USA 86:5473-5477), pancreas-specific promoters (Edlund et al. (1985) Science 230:912-916), and mammary gland-specific promoters. Developmentally-regulated promoters are also encompassed, for example the murine hox promoters (Kessel and Gruss (1990) Science 249:374-379) and the .alpha.-fetoprotein promoter (Campes and Tilghman (1989) Genes Dev. 3:537-546).

Also useful in the methods of the invention are recombinant expression vectors comprising the target gene nucleic acid molecule cloned into the expression vector in an antisense orientation. That is, the DNA molecule is operatively linked to a regulatory sequence in a manner which allows for expression (by transcription of the DNA molecule) of an RNA molecule which is antisense to the target gene mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes See Weintraub et al., Reviews—Trends in Genetics, Vol. 1(1) 1986.

Host cells into which the target gene expression vector has been introduced are useful in certain metods of the invention. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, the target gene protein can be expressed in bacterial cells such as E. col, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding the target gene or can be introduced on a separate vector. Cells stably transfected with the introduced nucleic acid can be identified by drug selection (e.g., cells that have incorporated the selectable marker gene will survive, while the other cells die)

A prokaryotic or eukaryotic host cell in culture can be used to produce (i.e., express) the target gene protein, e.g., by culturing the host cell (into which a recombinant expression vector encoding the target gene has been introduced) in a suitable medium such that the target gene protein is produced. The target gene protein can then be isolated from the medium or the host cell.

Host cells which are capable of expressing the target gene can also be used to produce nonhuman transgenic animals. For example, in one embodiment, a host cell of the invention is a fertilized oocyte or an embryonic stem cell into which the target gene-coding sequences have been introduced. Such host cells can then be used to create non-human transgenic animals in which exogenous the target gene sequences have been introduced into their genome or homologous recombinant animals in which endogenous the target gene sequences have been altered. Such animals are useful for studying the function and/or activity of the target gene and for identifying and/or evaluating modulators of the target gene activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous the target gene has been altered by homologous recombination between the endogenous gene and an exogenous DNA molecule introduced into a cell of the animal, e.g., an embryonic cell of the animal, prior to development of the animal.

A transgenic animal can be created by introducing the target gene-encoding nucleic acid into the male pronuclei of a fertilized oocyte, e.g., by microinjection, retroviral infection, and allowing the oocyte to develop in a pseudopregnant female foster animal. The target gene cDNA sequence can be introduced as a transgene into the genome of a non-human animal. Alternatively, a nonhuman homologue of the human the target gene such as a mouse the target gene, can be isolated based on hybridization to the human the target gene cDNA and used as a transgene. Intronic sequences and polyadenylation signals can also be included in the transgene to increase the efficiency of expression of the transgene. A tissue-specific regulatory sequence(s) can be operably linked to the target gene transgene to direct expression of the target gene protein to particular cells. Methods for generating transgenic animals via embryo manipulation and microinjection, particularly animals such as mice, have become conventional in the art and are described in Hogan, Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the target gene transgene in its genome and/or expression of the target gene mRNA in tissues or cells of the animals. A transgenic founder animal can then be used to breed additional animals carrying the transgene. Moreover, transgenic animals carrying a transgene encoding the target gene can further be bred to other transgenic animals carrying other transgenes.

To create a homologous recombinant animal, a vector is prepared which contains at least a portion of the target gene (e.g., a human or a non-human homolog of the target gene, e.g., a murine the target gene) into which a deletion, addition or substitution has been introduced to thereby alter, e.g., functionally disrupt, the target gene. In a preferred embodiment, the vector is designed such that, upon homologous recombination, the endogenous the target gene is functionally disrupted (i.e., no longer encodes a functional protein; also referred to as a "knock out" vector). Alternatively, the vector can be designed such that, upon homologous recombination, the endogenous the target gene is mutated or otherwise altered but still encodes functional protein (e.g., the upstream regulatory region can be altered to thereby alter the expression of the endogenous the target gene protein). In the homologous recombination vector, the altered portion of the target gene is flanked at its 5' and 3' ends by additional nucleic acid of the target gene to allow for homologous recombination to occur between the exogenous the target gene carried by the vector and an endogenous the target gene in an embryonic stem cell. The additional flanking the target gene nucleic acid is of sufficient length for successful homologous recombination with the endogenous gene. Typically, several kilobases of flanking DNA (both at the 5' and 3' ends) are included in the vector (see e.g., Thomas and Capecchi (1987) Cell 51:503 for a description of homologous recombination vectors). The vector is introduced into an embryonic stem cell line (e.g., by electroporation) and cells in which the introduced the target gene has homologously recombined with the endogenous the target gene are selected (see e.g., Li et al. (1992) Cell 69:915). The selected cells are then injected into a blastocyst of an animal (e.g., a mouse) to form aggregation chimeras (see, e.g., Bradley in Teratocarcinomas and Embryonic Stem Cells: A Practical Approach, Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) Current Opinion in Bio/Technology 2:823-829.

Transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232-6236. Another example of a recombinase system is the FLP recombinase system of Saccharomyces cerevisiae (O'Gorman et al. (1991) Science 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) Nature 385:810-813. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

Pharmaceutical Compositions

The target gene proteins, and anti-target gene antibodies, and modulators of the target gene expression or activity (also referred to herein as "active compounds") can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof;

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The target gene nucleic acid molecules of the invention can be inserted into vectors and used as gene therapy vectors. Gene therapy vectors can be delivered to a subject by, for example, intravenous injection, local administration or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

Uses and Methods of the Invention

The classifier, target gene nucleic acid molecules (identified or to be identified with the use of the invention), proteins, protein homologues, and antibodies described herein can be used in screening assays, predictive medicine (e.g., diagnostic assays, prognostic assays, monitoring clinical trials, and pharmacogenomics), and methods of treatment (e.g., therapeutic treatment methods and prophylactic treatment methods).

Screening Assays

The invention provides a method (also referred to herein as a "screening assay") for identifying molecular targets against which modulators can be developed, i.e., candidate or test compounds or agents (e.g., peptides, peptidomimetics, small molecules or other drugs) which bind to the target gene proteins or have a stimulatory or inhibitory effect on, for example, the target gene expression or the target gene activity. Such identified compounds may be useful for the modulation of radiation sensitivity/response. In one embodiment, the invention provides assays for screening candidate targets against which compounds, or other therapeutic agents, can be directed. The compounds used in conjunction with the present invention can be obtained using any of the numerous approaches in combinatorial library methods known in the art, including: biological libraries; natural products libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds may be presented in solution (e.g., Houghten (1992) Bio/Techniques 13:412-421), or on beads (Lam (1991) Nature 354:82-84), chips (Fodor (1993) Nature 364:555-556), bacteria, spores, plasmids (Cull et al. (1992) Proc. Natl. Acad. Sci. USA 89:1865-1869) or on phage (Scott and Smith (1990) Science 249:386-390; Devlin (1990) Science 249:404-406; Cwirla et al. (1990) Proc. Natl. Acad. Sci. 87:6378-6382; and Felici (1991) J. Mol: Biol. 222:301-310).

In one embodiment, an assay is a cell-based assay in which a cell which expresses the target gene protein, or a biologically active portion thereof, is contacted with a test compound and the ability of the test compound to bind to the target gene protein determined. The cell, for example, can be a yeast cell or a cell of mammalian origin. Determining the ability of the test compound to bind to the target gene protein can be accomplished, for example, by coupling the test compound with a radioisotope or enzymatic label such that binding of the test compound to the target gene protein or biologically active portion thereof can be determined by detecting the labeled compound in a complex. For example, test compounds can be labeled with $^{125}I$, $^{35}C$, $^{14}C$, or $^{3}H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses the target gene protein, or a biologically active portion thereof, with a known compound which binds the target gene to form an assay mixture, contacting the assay mixture with a test compound, and determining the ability of the test compound to interact with the target gene protein, wherein determining the ability of the test compound to interact with the target gene protein comprises determining the ability of the test compound to preferentially bind to the target gene or a biologically active portion thereof as compared to the known compound.

In another embodiment, an assay is a cell-based assay comprising contacting a cell expressing the target gene protein, or a Biologically active portion thereof, with a test compound and determining the ability of the test compound to modulate (e.g., stimulate or inhibit) the activity of the target gene protein or biologically active portion thereof. Determining the ability of the test compound to modulate the activity of the target gene or a biologically active portion thereof can be accomplished, for example, by determining the ability of the target gene protein to bind to or interact with the target gene molecule of interest. As used herein, a "molecule of interest" is a molecule with which the target gene protein binds or interacts in nature, for example, a molecule in the nucleus or cytoplasm of a cell which expresses the target gene protein. The target gene molecule of interest can be a non-the target gene molecule or the target gene protein or polypeptide. The target, for example, can be a second intracellular protein which has catalytic activity, a protein which naturally binds to the target gene protein, or a protein which facilitates the association of DNA with the target gene.

Determining the ability of the target gene protein to bind to or interact with the target gene molecule of interest can be accomplished by one of the methods described above for determining direct binding. In a preferred embodiment, determining the ability of the target gene protein to bind to or interact with a target gene molecule of interest can be accomplished by determining the activity of the molecule of interest or detecting a cellular response, for example, cell survival or cell proliferation in the presence of a chemotherapeutic drug.

In yet another embodiment, an assay of the present invention is a cell-free assay comprising contacting the target gene protein or biologically active portion thereof with a test compound and determining the ability of the test compound to bind to the target gene protein or biologically active portion thereof. Binding of the test compound to the target gene protein can be determined either directly or indirectly as described above. In one embodiment, the assay includes contacting the target gene protein or biologically active portion thereof with a known compound which binds the target gene to form an assay mixture, contacting the assay mixture with a test compound, and determining the ability of the test compound to interact with the target gene protein, wherein determining the ability of the test compound to interact with the target gene protein comprises determining the ability of the test compound to preferentially bind to the target gene or biologically active portion thereof as compared to the known compound.

In another embodiment, an assay is a cell-free assay comprising contacting the target gene protein or biologically active portion thereof with a test compound and determining the ability of the test compound to modulate (e.g., stimulate or inhibit) the activity of the target gene protein or biologically active portion thereof. Determining the ability of the test compound to modulate the activity of the target gene can be accomplished, for example, by determining the ability of the target gene protein to bind to the target gene molecule of interest by one of the methods described above for determining direct binding. In an alternative embodiment, determining the ability of the test compound to modulate the activity of the target gene can be accomplished by determining the ability of the target gene protein further modulate the target gene molecule of interest. For example, the catalytic/enzymatic activity of the molecule of interest on an appropriate substrate can be determined as previously described.

In yet another embodiment, the cell-free assay comprises contacting the target gene protein or biologically active portion thereof with a known compound which binds the target gene to form an assay mixture, contacting the assay mixture with a test compound, and determining the ability of the test compound to interact with the target gene protein, wherein determining the ability of the test compound to interact with the target gene protein comprises determining the ability of the target gene protein to preferentially bind to or modulate the activity of the target gene molecule of interest.

The cell-free assays of the present invention are amenable to use of both native and variant forms (e.g., peptide fragments and fusion proteins) of the target gene. In the case of cell-free assays comprising a hydrophobic form of the target gene, it may be desirable to utilize a solubilizing agent such that the hydrophobic form of the target gene is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either the target gene or its molecule of interest to facilitate separation of complexed from uncomplexed forms of one or both of the proteins, as well as to accommodate automation of the assay. Binding of a test compound to the target gene, or interaction of the target gene with a molecule of interest in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/the target gene fusion proteins or glutathione-S-transferase/target fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or the target gene protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of the target gene binding or activity determined using standard techniques.

Other techniques for immobilizing proteins on matrices can also be used in the screening assays of the invention. For example, either the target gene or its molecule of interest can be immobilized utilizing conjugation of biotin and streptavidin. Biotinylated the target gene or molecule of interests can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical).

Alternatively, antibodies reactive with the target gene or molecule of interests but which do not interfere with binding of the target gene protein to its molecule of interest can be derivatized to the wells of the plate, and unbound target or the target gene trapped in the wells by antibody conjugation. Methods for detecting such complexes, in addition to those described above for the GST-immobilized complexes, include immunodetection of complexes using antibodies reactive with the target gene or molecule of interest, as well as enzyme-linked assays which rely on detecting an enzymatic activity associated with the target gene or molecule of interest.

In another embodiment, modulators of the target gene expression are identified in a method in which a cell is contacted with a candidate compound and the expression of the target gene (mRNA or protein, or the copy number of the target gene) in the cell is determined. The level of expression of the target gene in the presence of the candidate compound is compared to the level of expression of the target gene in the absence of the candidate compound. The candidate compound can then be identified as a modulator of the target gene expression based on this comparison. For example, when expression of the target gene mRNA or protein is greater (statistically significantly greater) in the presence of the candidate compound than in its absence, the candidate compound is identified as a stimulator of the target gene mRNA or protein expression. Alternatively, when expression of the target gene mRNA or protein is less (statistically significantly less) in the presence of the candidate compound than in its absence, the candidate compound is identified as an inhibitor of the target gene mRNA or protein expression. The level of the target gene mRNA or protein expression in the cells, or the number of the target gene copies per cell can be determined by methods described herein for detecting the target gene genomic DNA, mRNA, or protein.

the target gene proteins can be used as "bait proteins" in a two-hybrid assay or three hybrid assay (see, e.g., Zervos et al. (1993) Cell 72:223-232; Madura et al. (1993) J. Biol. Chem. 268:12046-12054; Bartel et al. (1993) Dio/Techniques 14:920-924; Iwabuchi et al. (1993) Oncogene 8:1693-1696; and W094/10300), to identify other proteins, which bind to or interact with the target gene ("the target gene-binding proteins" or "the target gene-bp") and modulate the target gene activity.

The two-hybrid system is based on the modular nature of most transcription factors, which consist of separable DNA-binding and activation domains. Briefly, the assay utilizes two different DNA constructs. In one construct, the target gene is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a target gene-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the target gene.

This invention further pertains to novel agents identified by the above-described screening assays and uses thereof for treatments as described herein.

Predictive Medicine

The present invention also pertains to the field of predictive medicine in which diagnostic assays, imaging tests, prognostic assays, pharmacogenomics, and monitoring clinical trials are used for prognostic (predictive) purposes to thereby treat an individual prophylactically. Accordingly, one aspect of the present invention relates to diagnostic assays for determining the target gene protein and/or nucleic acid expression as well as the target gene activity, in the context of a biological sample (e.g., blood, serum, cells, tissue) to thereby determine whether an individual is afflicted with a disease or disorder, or is at risk of developing a disorder, associated with aberrant target gene expression or activity (e.g., altered radiation resistance). The invention also provides for prognostic (or predictive) assays for determining whether an individual is at risk of developing a disorder associated with the target gene protein, nucleic acid expression or activity (e.g., altered drug resistance). For example, mutations in the target gene can be assayed in a biological sample. Such assays can be used for prognostic or predictive purpose to thereby prophylactically treat an individual prior to the onset of a disorder characterized by or associated with the target gene protein, nucleic acid expression or activity. For example, because the target gene is expressed at a higher level in radiation sensitive cells than non-drug resistant cell lines, higher than normal expression of the target gene can be used as an indicator of radiation sensitivity.

Another aspect of the invention provides methods for determining the target gene protein, nucleic acid expression or the target gene activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent).

Yet another aspect of the invention pertains to monitoring the influence of agents (e.g., drugs or other compounds) on the expression or activity of the target gene in clinical trials. These and other agents are described in further detail in the following sections.

Diagnostic Assays

The invention provides a method of assessing expression, especially desirable expression, of a cellular the target gene. The excessive expression of a classieier may indicate the presence, persistence or reappearance of radiation sensitive tumor cells in an individual's tissue. More generally, aberrant expression may indicate the occurrence of a deleterious or disease-associated phenotype contributed to by the target gene.

An exemplary method for detecting the presence or absence of the target gene in a biological sample involves obtaining a biological sample (preferably from a body site implicated in a possible diagnosis of diseased or malignant tissue) from a test subject and contacting the biological sample with a compound or an agent capable of detecting the target gene protein or nucleic acid (e.g., mRNA, genomic DNA) that encodes the target gene protein such that the presence of the target gene is detected in the biological sample.

The lack and/or relative low expression of the target gene indicates aberrant or undesirable expression of the target gene, and correlates with the occurrence in situ of cells having a radiation-resistant phenotype.

A preferred agent for detecting the target gene mRNA or genomic DNA is a labeled nucleic acid probe capable of hybridizing to the target gene mRNA or genomic DNA. The nucleic acid probe can be, for example, a full-length the target gene nucleic acid or a portion thereof, such as an oligonucleotide of at least 15, 30, 50, 100, 250 or 500 nucleotides in length and sufficient to specifically hybridize under stringent conditions to the target gene mRNA or genomic DNA. Other suitable probes for use in the diagnostic assays of the invention are described herein.

A preferred agent for detecting the target gene protein is an antibody capable of binding to the target gene protein, preferably an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect the target gene mRNA, protein, or genomic DNA in a biological sample in vitro as well as in vivo. For example, in vitro techniques for detection of the target gene mRNA include Northern hybridizations and in situ hybridizations. In vitro techniques for detection of the target gene protein include enzyme linked immunosorbent assays (ELISAs), Western blots, immunoprecipitations and immunofluorescence. In vitro techniques for detection of the target gene genomic DNA include Southern hybridizations.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting the target gene protein, mRNA, or genomic DNA, such that the presence of the target gene protein, mRNA or genomic DNA is detected in the biological sample, and comparing the presence of the target gene protein, mRNA or genomic DNA in the control sample with the presence of the target gene protein, mRNA or genomic DNA in the test sample.

The invention also encompasses kits for detecting the presence of the target gene in a biological sample (a test sample). Such kits can be used to determine if a subject is suffering from or is at increased risk of developing a disorder associated with aberrant expression of the target gene (e.g., the presence of a drug resistance cancer). For example, the kit can comprise a labeled compound or agent capable of detecting the target gene protein or mRNA in a biological sample and means for determining the amount of the target gene in the sample (e.g., an anti-the target gene antibody or an oligonucleotide probe which binds to DNA encoding the target gene. Kits may also include instruction for observing that the tested subject is suffering from or is at risk of developing a disorder associated with aberrant expression of the target gene if the amount of the target gene protein or mRNA is above or below a normal level.

For antibody-based kits, the kit may comprise, for example: (1) a first antibody (e.g., attached to a solid support) which binds to the target gene protein; and, optionally, (2) a second, different antibody which binds to the target gene protein or the first antibody and is conjugated to a detectable agent.

For oligonucleotide-based kits, the kit may comprise, for example: (1) a oligonucleotide, e.g., a detectably labelled oligonucleotide, which hybridizes to the target gene nucleic acid sequence or (2) a pair of primers useful for amplifying the target gene nucleic acid molecule;

The kit may also comprise, e.g., a buffering agent, a preservative, or a protein stabilizing agent. The kit may also comprise components necessary for detecting the detectable agent (e.g., an enzyme or a substrate). The kit may also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of the target gene.

Prognostic Assays

The methods described herein can furthermore be utilized as diagnostic or prognostic assays to identify subjects having or at risk of developing a disease or disorder associated with aberrant target gene expression or activity. For example, the assays described herein, such as the preceding diagnostic assays or the following assays, can be utilized to identify a subject having or at risk of developing a disorder associated with aberrant target gene protein, nucleic acid expression or activity (eg., the presence of radiation resistant tumor cells). Alternatively, the prognostic assays can be utilized to identify a subject having or at risk for developing such a disease or disorder. Thus, the present invention provides a method in which a test sample is obtained from a subject and the target gene protein or nucleic acid (e.g., mRNA, genomic DNA) is detected, wherein the presence or relative quantity of the target gene protein or nucleic acid is diagnostic for a subject having or at risk of developing a disease or disorder associated with aberrant target gene expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant target gene expression or activity. Thus, if decreased target gene expression is a cause of increased drug resistance, such methods can be used to determine whether a subject can be effectively treated with a specific agent or class of agents (e.g., agents of a type which increase the target gene activity). Thus, the present invention provides methods for determining whether a subject can be effectively treated with an agent for a disorder associated with aberrant target gene expression or activity in which a test sample is obtained and the target gene protein or nucleic acid is detected (e.g., wherein the presence or relative quantity of the target gene protein or nucleic acid is diagnostic for a subject that can be administered the agent to treat a disorder associated with aberrant target gene expression or activity). In some embodiments, the foregoing methods provide information useful in prognostication, staging and management of malignancies (tumors) that are characterized by altered expression of the target gene and thus by a radiation-resistant phenotype. The information more specifically assists the clinician in designing radiation therapy or other treatment regimes to eradicate such malignancies from the body of an afflicted subject.

The methods of the invention can also be used to detect genetic lesions (e.g., mutations or amplifications) in the target gene, thereby determining if a subject with the altered gene is at risk for a disorder characterized by aberrant cell proliferation and/or differentiation. For example, genetic mutations, whether of germline or somatic origin, may indicate whether the process of developing radiation resistance has been initiated or is likely to arise in the tested cells. In preferred embodiments, the methods include detecting, in a sample of cells from the subject, the presence or absence of a genetic lesion characterized by at least one of an alteration affecting the integrity of a gene encoding the target gene-protein, the mis-expression of the target gene, or the amplification of the target gene. Preferably the sample of cells is obtained from a body tissue suspected of comprising transformed cells (e.g., cancer cells). Thus, the present method provides information relevant to diagnosis of the presence of a tumor.

Genetic lesions can be detected, for example, by ascertaining the existence of at least one of 1) a deletion of one or more nucleotides from the target gene; 2) an addition of one or more nucleotides to the target gene; 3) a substitution of one or more nucleotides of the target gene, 4) a chromosomal rearrangement of the target gene; 5) an alteration in the level of a messenger RNA transcript of the target gene, 6) aberrant modification of the target gene, such as of the methylation pattern of the genomic DNA, 7) the presence of a non-wild type splicing pattern of a messenger RNA transcript of the target gene, 8) a non-wild type level of the target gene-protein, 9) allelic loss of the target gene, 10) amplification of the target gene, and 11) inappropriate post-translational modification of the target gene-protein. As described herein, there are a large number of assay techniques known in the art which can be used for detecting lesions in the target gene. A preferred biological sample is a biopsy sample of tissue suspected of comprising transformed cells isolated by conventional means from a subject.

In certain embodiments, detection of the lesion involves the use of a probe/primer in a polymerase chain reaction (PCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in the target gene (see Abravaya et al. (1995) Nucleic Acids Res. 23:675-682). This method can include the steps of collecting a sample of cells from a patient, isolating nucleic acid (e.g., genomic, mRNA or both) from the cells of the sample, contacting the nucleic acid sample with one or more primers which specifically hybridize to the target gene under conditions such that hybridization and amplification of the target gene -gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (Guatelli et al. (1990) Proc. Natl. Acad. Sci. USA 87:1874-1878), transcriptional amplification system (Kwoh, et al. (1989) Proc. Natl. Acad. Sci. USA 86:1173-1177), Q-Beta Replicase (Lizardi et al. (1988) Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in the target gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes can be used to score for the presence of specific mutations by development or loss of a ribozyme cleavage site.

In other embodiments, genetic mutations in the target gene can be identified by hybridizing a sample and control nucleic acids, e.g., DNA or RNA, to high density arrays containing hundreds or thousands of oligonucleotides probes (Cronin et al. (1996) Human Mutation 7:244-255; Kozal et al. (1996) Nature Medicine 2:753-759). For example, genetic mutations in the target gene can be identified in two-dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the target gene and detect mutations by comparing the sequence of the sample the target gene with the corresponding wild-type (control) sequence. Additionally, sequencing of the DNA flanking the target gene can be used to determine if the target gene has been amplified. Examples of sequencing reactions include those based on techniques developed by Maxim and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Bio/Techniques 19:448), including sequencing by mass spectrometry (see, e.g., Adv. Chromatogr. 36:127-162; and Griffin et al. (1993) Appl. Biochem. Biotechnol. 38:147-159).

Other methods for detecting mutations in the target gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes of formed by hybridizing (labeled) RNA or DNA containing the wild-type target gene sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al (1988) Proc. Natl Acad Sci USA 85:4397; Saleeba et al (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in the target gene cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) Carcinogenesis 15:1657-1662). According to an exemplary embodiment, a probe based on the target gene sequence, e.g., a wild-type target gene sequence, is hybridized to a cDNA or other DNA product from a test cell(s). The duplex is treated with a DNA mismatch repair enzyme, and the cleavage products, if any, can be detected from electrophoresis protocols or the like.

In other embodiments, alterations in electrophoretic mobility will be used to identify mutations in the target genes. For example, single strand conformation polymorphism (SSCP) may be used to detect differences in electrophoretic mobility between mutant and wild type nucleic acids (Orita et al. (1989) Proc Natl. Acad. Sci USA: 86:2766, see also Cotton (1993) Mutat. Res. 285:125-144; and Hayashi (1992) Genet Anal Tech Appl 9:73-79). Single-stranded DNA fragments of sample and control the target gene nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet 7:5).

In yet another embodiment, the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al. (1989) Proc. Natl Acad. Sci USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238). In addition, it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving the target gene.

Furthermore, any cell type or tissue, preferably biopsy samples of tissue comprising or suspected of comprising transformed cells, in which the target gene is expressed may be utilized in the prognostic assays described herein.

Pharmacogenomics

Agents or modulators which have a stimulatory or inhibitory effect on the target gene activity (e.g., the target gene expression) as identified by a screening assay described herein can be administered to individuals to treat (prophylactically or therapeutically) disorders (e.g., radiation-resistance) associated with aberrant target gene activity. In conjunction with such treatment, the pharmacogenomics (i.e., the study of the relationship between an individual's genotype and that individual's response to a foreign compound or radiation) of the individual may be considered. Differences in metabolism of therapeutics can lead to severe toxicity or therapeutic failure by altering the relation between dose and blood concentration of the radiation therapy. Thus, the pharmacogenomics of the individual permits the selection of effective treatmentss (e.g., radiation) for prophylactic or therapeutic treatments based on a consideration of the individual's genotype. Such pharmacogenomics can further be used to determine appropriate dosages and therapeutic regimens. Accordingly, the activity of the target gene protein, expression of the target gene nucleic acid, or mutation content of the target genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) Clin. Chem. 43(2): 254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of the target gene protein, expression of the target gene nucleic acid, or mutation content of the target genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with the target gene modulator, such as a modulator identified by one of the exemplary screening assays described herein.

Monitoring of Effects During Clinical Trials

Monitoring the influence of agents (e.g., drugs, compounds) on the expression or activity of the target gene (e.g., the ability to modulate the drug-resistant phenotype of a cell) can be applied not only in basic drug screening, but also in clinical trials. For example, the effectiveness of an agent determined by a screening assay as described herein to increase the target gene expression, protein levels, or down-regulate the target gene activity, can be monitored in clinical trails of subjects exhibiting increased the target gene expression, protein levels, or upregulated the target gene activity.

Alternatively, the effectiveness of an agent determined by a screening assay to increase the target gene expression, protein levels, or upregulate the target gene activity (e.g., to decrease the radiation sensitivity of a non-cancerous cell), can be monitored in clinical trials of compounds designed to decrease the target gene expression, protein levels, or down-regulate the target gene activity. In such clinical trials, the expression or activity of the target gene and, preferably, other genes that have been implicated in, for example, a cellular proliferation disorder, can be used as a "read out" or markers of the radiation sensitivity of a particular cell.

For example, and not by way of limitation, genes, including the target gene, that are modulated in cells by treatment with an agent (e.g., compound, drug or small molecule) which modulates the target gene activity (e.g., identified in a screening assay as described herein) can be identified. Thus, to study the effect of agents on cellular proliferation disorders, for example, in a clinical trial, cells can be isolated and RNA prepared and analyzed for the levels of expression of the target gene or other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of the target gene or other genes. In this way, the gene expression pattern can serve as a marker, indicative of the physiological response of the cells to the agent. Accordingly, this response state may be determined before, and at various points during, treatment of the individual with the radiation therapy.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the treatment; (ii) detecting the level of expression of the target gene protein, mRNA, or genomic DNA in the preadministration sample; (iii) obtaining one or more post-administration samples from the subject; (iv) detecting the level of expression or activity of the target gene protein, mRNA, or genomic DNA in the post-administration samples; (v) comparing the level of expression or activity of the target gene protein, mRNA, or genomic DNA in the pre-administration sample with the target gene protein, mRNA, or genomic DNA in the post administration sample or samples; and (vi) altering the administration of the treatment to the subject accordingly. For example, increased administration of the agent may be desirable to decrease the expression or activity of the target gene to higher levels than detected, i.e., to increase the effectiveness of the treatment.

Methods of Treatment

The present invention provides for both prophylactic and therapeutic methods of treating a subject at risk of (or susceptible to) a disorder or having a disorder associated with aberrant target gene expression or activity. Such disorders include cellular resistance to radiation therapy.

Prophylactic Methods

In one aspect, the invention provides a method for preventing in a subject, a disease or condition associated with an aberrant target gene expression or activity (e.g., the development of radiation resistance), by administering to the subject an agent which modulates the target gene expression or at least one target gene activity. Subjects at risk for a condition which is caused or contributed to by aberrant target gene expression or activity can be identified by, for example, any or a combination of diagnostic or prognostic assays as described herein. Administration of a prophylactic agent can occur prior to the manifestation of symptoms characteristic of the target gene aberrancy, such that a disease or disorder is prevented or, alternatively, delayed in its progression. For example, administration of a prophylatic agent to a cancer patient may prevent or delay the development of radiation resistance in the patient's cancer cells. Depending on the type of the target gene aberrancy, for example, the target gene agonist or the target gene antagonist agent can be used for treating the subject. The appropriate agent can be determined based on screening assays described herein.

Therapeutic Methods

Another aspect of the invention pertains to methods of modulating the target gene expression or activity for therapeutic purposes. For example, the effectiveness of radiation therapy is "potentiated" (enhanced) by restoring or improving vulnerability of the transformed cells to the cytotoxic effects of radiation that otherwise would be less effective by reducing the expression of the target gene in the cells. The modulatory method of the invention involves contacting a cell with an agent that modulates one or more of the activities of the target gene protein activity associated with the cell. An agent that modulates the target gene protein activity can be an agent as described herein, such as a nucleic acid or a protein, a naturally-occurring cognate ligand of the target gene protein, a peptide, the target gene peptidomimetic, or other small molecule. In one embodiment, the agent stimulates one or more of the biological activities of the target gene protein. Examples of such stimulatory agents include active the target gene protein and a nucleic acid molecule encoding the target gene that has been introduced into the cell. In another embodiment, the agent inhibits one or more of the biological activities of the target gene protein. Examples of such inhibitory agents include antisense the target gene nucleic acid molecules and anti-the target gene antibodies. These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of the target gene protein or nucleic acid molecule. In one embodiment, the method involves administering an agent (e.g., an agent identified by a screening assay described herein), or combination of agents that modulates (e.g., upregulates or downregulates) the target gene expression or activity. In another embodiment, the method involves administering the target gene protein or nucleic acid molecule as therapy to compensate for reduced or aberrant target gene expression or activity.

For example, in one embodiment, the method involves administering a desired drug to an individual afflicted with a radiation-resistant cell population (a tumor, e.g., a carcinoma, sarcoma, leukemia, lymphoma, or lymphosarcoma), and coadministering a stumlator of the target gene expression or activity. The administration and coadministration steps can be carried out concurrently or in any order, and can be separated by a time interval sufficient to allow uptake of either compound by the cells to be eradicated. For example, an antisense pharmaceutical composition (or a cocktail composition comprising an the target gene antisense oligonucleotide in combination with one or more other antisense oligonucleotides) can be administered to the individual sufficiently in advance of administration of the radiation therapy to allow the antisense composition to permeate the individual's tissues, especially tissue comprising the transformed cells to be eradicated; to be internalized by transformed cells; and to modulate the target gene expression and/or protein production.

Stimulation of the target gene activity is desirable in situations in which the target gene is abnormally down-regulated and/or in which increased target gene activity is likely to have a beneficial effect, e.g., in increasing the radiation sensitivity of a cancer cell. Conversely, inhibition of the target gene activity is desirable in situations in which the target gene is abnormally up-regulated and/or in which decreased the target gene activity is likely to have a beneficial effect, e,g., in decreasing the radiation sensitivity of a non-cancer cell.

This invention is further illustrated by the following examples which should not be construed as limiting. The contents of all references, patents and published patent applications cited throughout this application are hereby incorporated by reference.

EXAMPLE I

The invention includes a classifier to predict cellular radiation sensitivity based on gene expression profiles in thirty-five cell lines from the NCI panel of 60 cancer cell lines (NCI-60), using a novel approach to predictive gene analysis. The classifier predicts, within 10%, the survival fraction value after 2 Grays (SF2) for twenty-two of the thirty-five cell lines for a 62% predictive accuracy. A permutation analysis shows that the likelihood of predicting 22 SF2s out of 35 samples within 10% by chance alone was 1 in 5,000 (p=0.0002). Furthermore, analysis identified three novel genes, retinoblastoma binding protein 4 (RbAp48), G-protein signaling regulator 19 (RGS19) and ribose-5-phosphate isomerase A (R5PIA) whose expression values are strongly correlated with radiation sensitivity. Moreover, gene selection analysis by performing quantitative real-time PCR of the selected genes, confirms the target geneexpression level as determined by the microarray. Finally classifier can be used to modulate the resistance of a cell to radiation, as shown by transfection of RbAp48 into HS-578T cells, a radioresistant cell line that displayed low baseline RbAp48 expression induced significant radiosensitization when compared to a mock-transfected cell line, as predicted by the classifier.

Development of a radiation classifier in the NCI panel of 60 cell lines (NCI-60)

The general scheme of the classifier is shown in FIG. 1. The approach adopted by the inventors utilized a subset of 35 cell lines from the NCI panel of 60 for which radiation sensitivity data as defined by survival fraction after 2 Gy (SF2) was either published in the literature (23 cell lines) or determined in our lab (12 cell lines). The baseline genomic expression for each of these cell lines was obtained from the study by Stauton[6] (Affymetrix HU-6800 microarrays, 7,129 genes, available at http://www-genome.wi.mit.edu/cgi-bin/cancer/publications/pubpaper.cgi?mode=view&paperid=59).

The design of the classifier involved two steps. An initial step (gene filtering), to identify only those genes that were predictive of radiation response. This was performed using SAM analysis (Significant Analysis of Microarrays). Statistical tests of correlation with a response variable are subject to significant loss of power due to the large number of multiple hypothesis (e.g. 7,129) being tested. In the SAM analysis, permutation analysis is performed to estimate the false discovery rate empirically. As shown in FIG. 1, the gene expression profile and radiation sensitivity parameter (SF2) for each cell line are used by SAM to identify the genes (output) correlated with the radiation parameter. To limit the potential genes that might be selected by this approach, the number of genes was chosen such that an estimated false discovery rate (FDR) of 5% was achieved. A permutation analysis (noise) was generated within the inventor's own dataset by creating one hundred random permutations of incorrect pairings of gene expression profiles and radiation sensitivity. SAM analysis was performed for these incorrectly paired samples as described above.

Only genes selected by the correct pairings and not selected by the incorrect pairing were further used in the classifier. Genes selected by both correct and incorrect pairings were disregarded.

The next step involved the evaluation of the classifier. This was performed by leave-one-out cross validation. This approach was chosen because it is a robust analytical process, useful when small numbers of samples are available. In this approach the samples are divided in 34 training samples and 1 test sample. Gene filtering as described above is performed using the 34 training samples and the genes selected are then used to build the classifier. The classifier is then evaluated using the test sample. The gene expression in the test sample of the SAM selected genes is provided to the classifier that then predicts its radiation sensitivity (SF2), using a multivariate linear regression approach. This process is repeated an additional 34 times so that each sample serves as the test sample once. SF2 is treated as a continuous variable and a prediction is deemed correct if it is within 10% of the actual reported average SF2 (for those cell lines obtained from the literature) or within the range of measured SF2s in our own experiments (occasionally more than 10%, in 4 of 35 cell lines).

EXAMPLE II

FIG. 6 and 7 show the results of the classifier. The classifier predicted 22/35 (62%) of the cell lines SF2 values correctly. A median and mean absolute difference of 0.104 and 0.157 respectively between the true and predicted SF2s was calculated. Thirteen samples were incorrectly classified. Of these, 2 samples missed their cutoff by less that 5%. These include cell lines KM 12 (Predicted SF2=0.56, True SF2=0.42, Cutoff=0.52) and SF 539 (Predicted SF2=0.677, True SF2=0.82, Cutoff=0.72). All three leukemia cell lines in the list (HL60, CCRF-CEM and MOLT4) were incorrectly classified as well. However for two of them (HL60 and CCRF-CEM), the predicted SF2 was a negative number (−0.014 and −0.133 respectively). Therefore, the classifier judged these two cell lines to be in the radiosensitive side of the spectrum, which is indeed true. However this failed to meet the criteria as originally defined and thus they were classified as incorrect predictions.

Figure 2A:
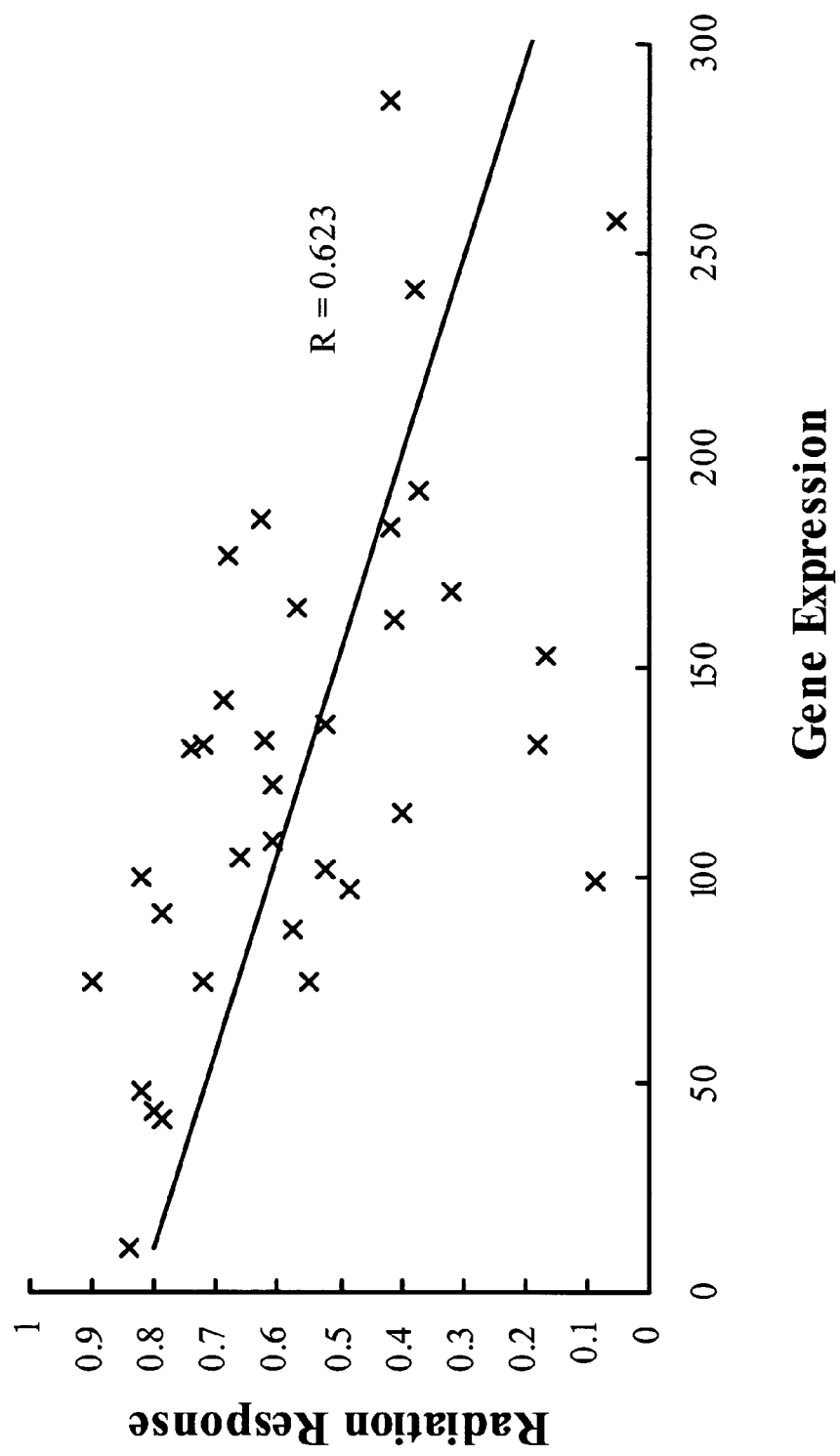
Figure 3A:
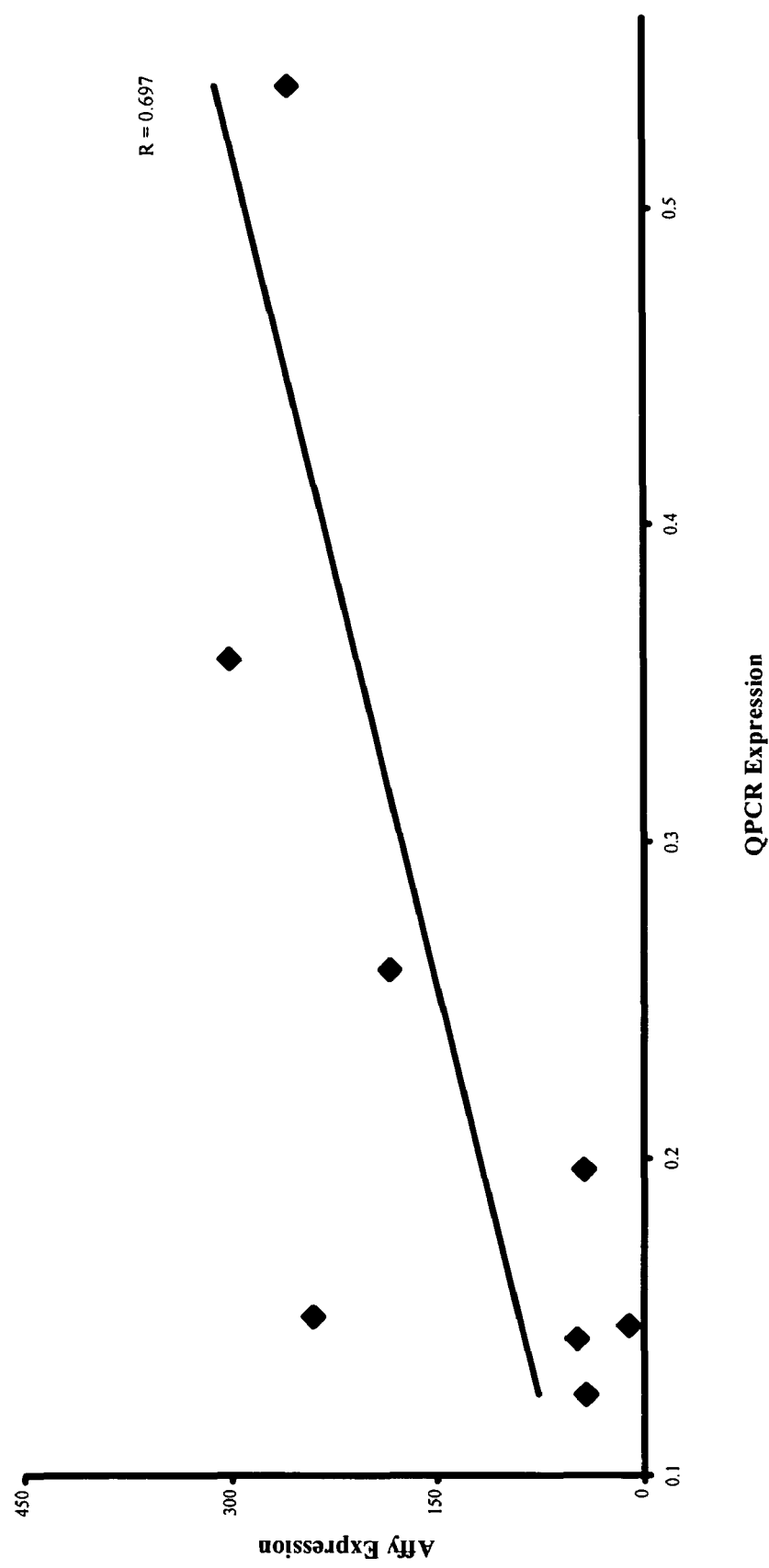
FIGS. 3A through F are a series of graphs depicting an excellent correlation between quantitative real-time PCR and microarrays for all three known genes selected by the analysis.
Figure 3B:
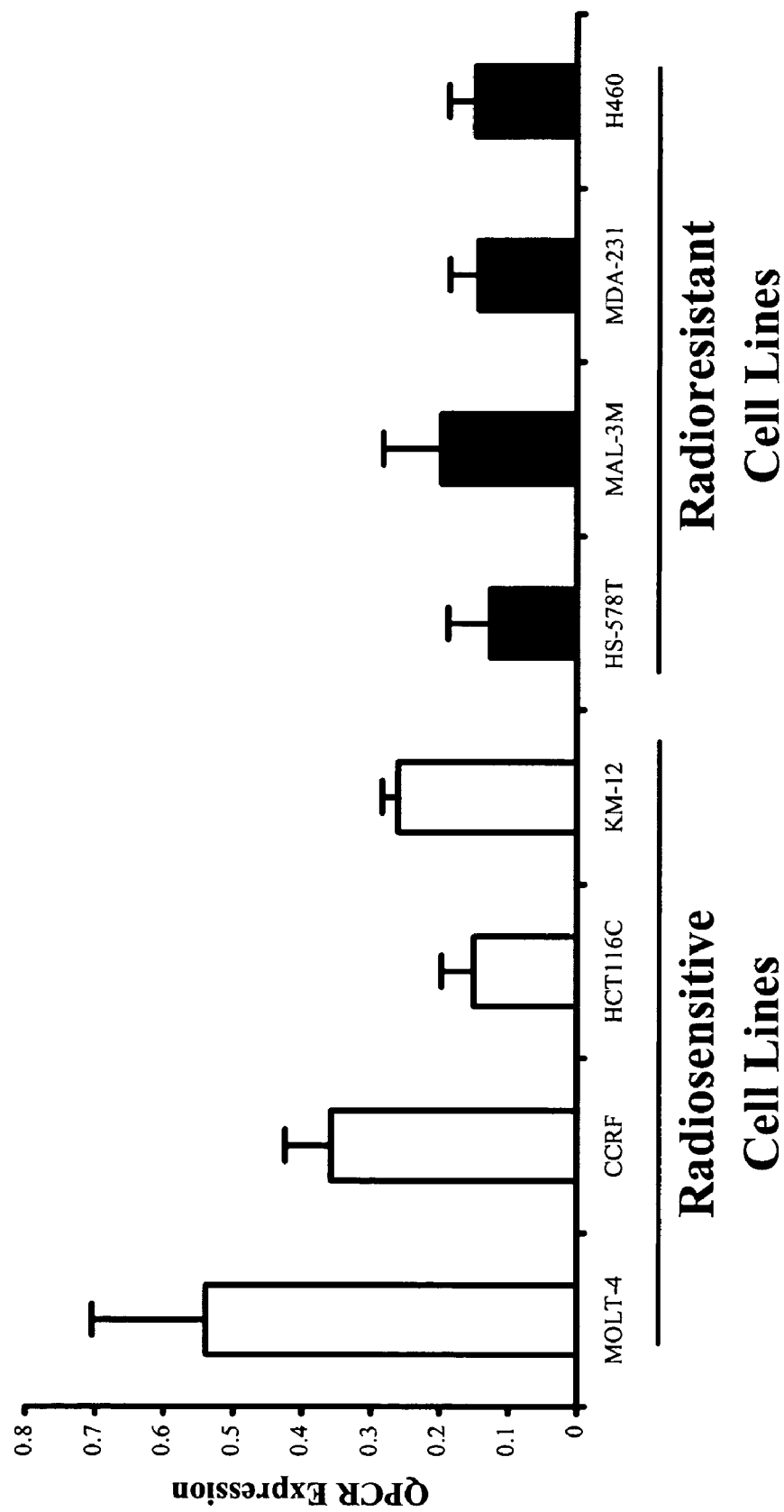
Figure 3C:
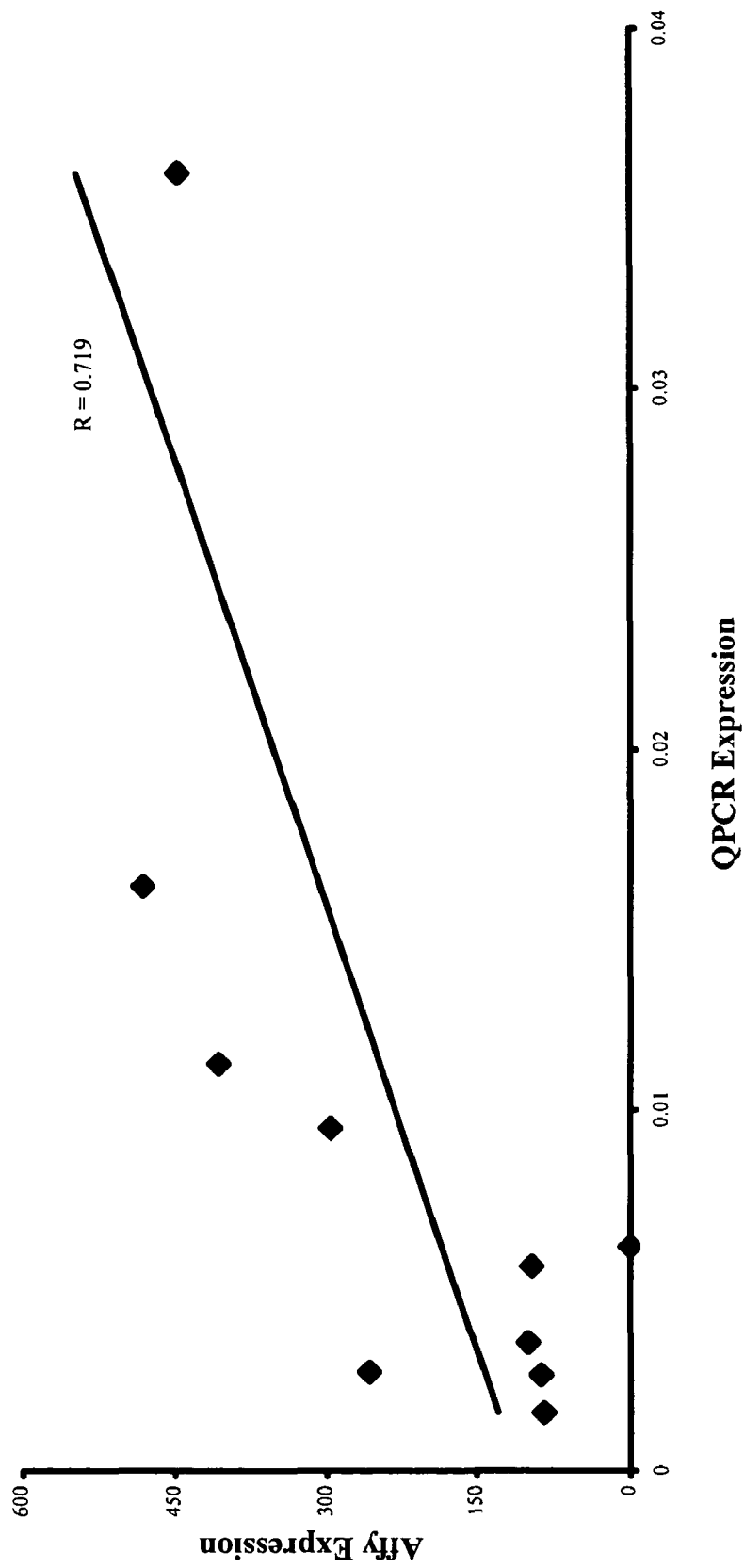
Figure 3D:
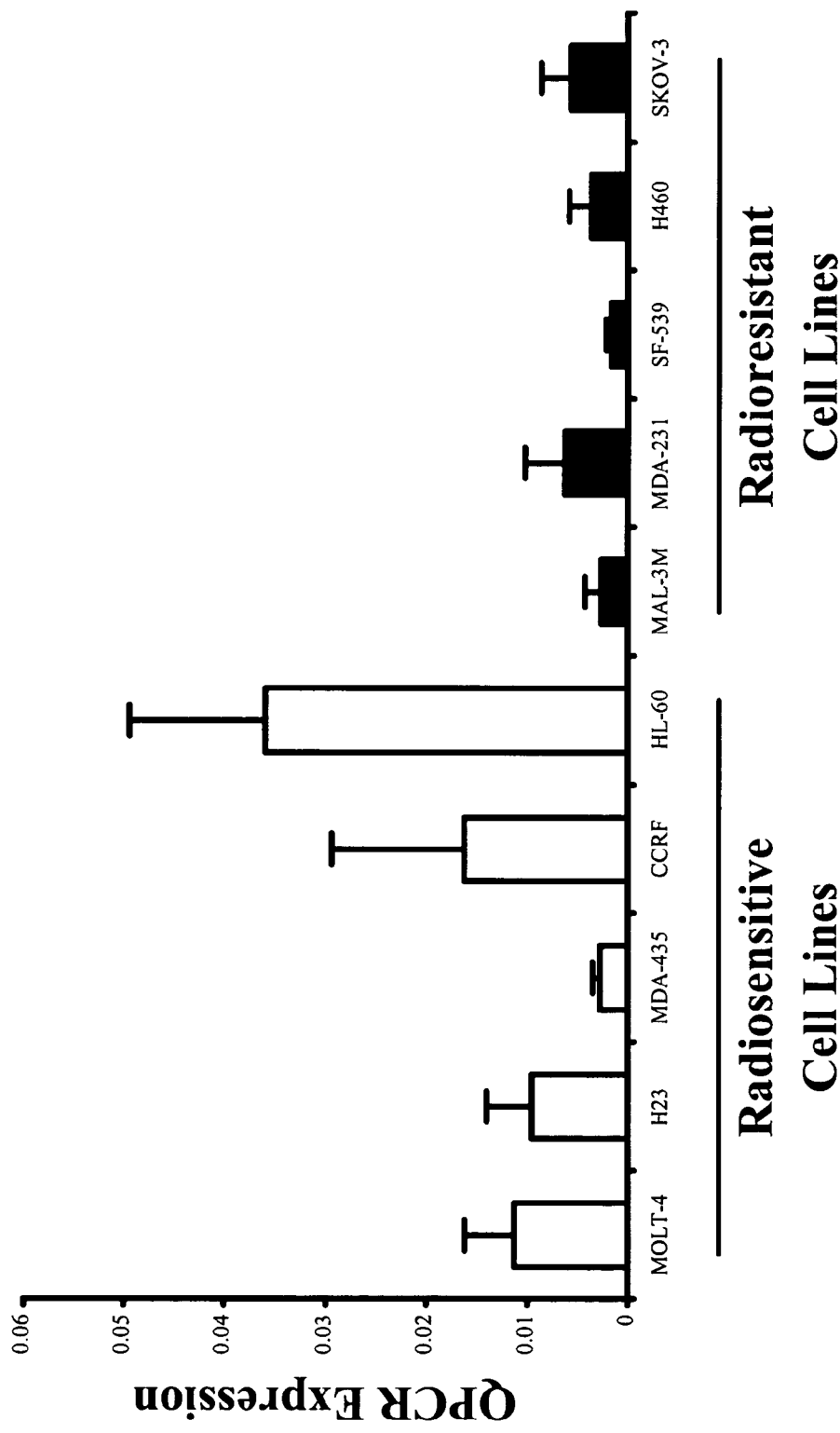
Figure 3E:
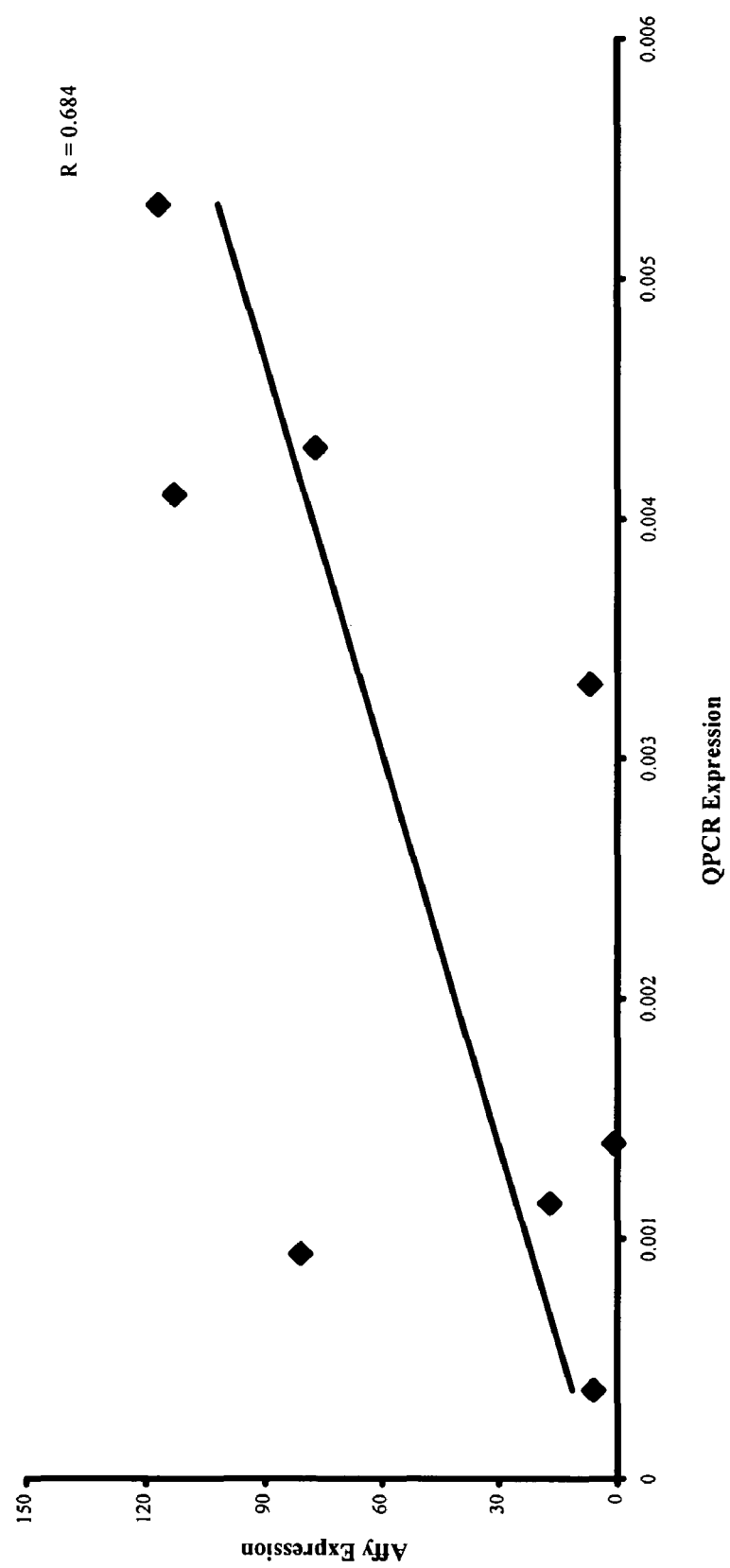
Figure 3F:
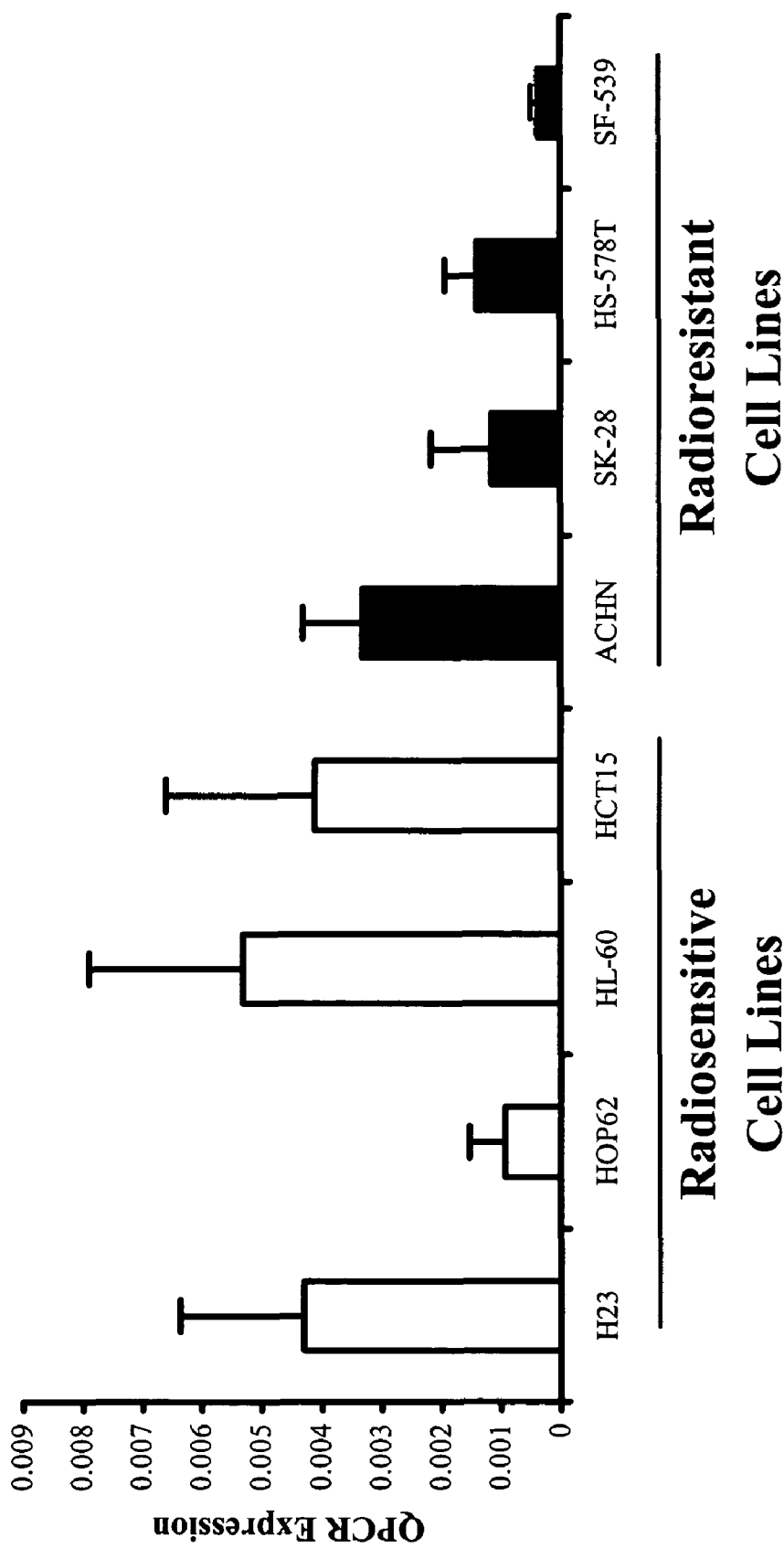

FIG. 8 shows the list of genes that were selected by SAM analysis to be predictive of radiation response. The four top genes were consistently selected by SAM through all or most of the 35 rounds of training. The genes include ribose 5-phosphate isomerase A (selected by SAM 35/35 times), retinoblastoma binding protein 4, also known as RbAp48 (selected by SAM 34/35 times), G protein signaling regulator 19 (selected by SAM 34/35 times) and an unknown gene (Affymetrix ID HG4236-HT4506, selected by SAM 33/35 times). FIG. 2 shows that there was a linear correlation between the expression values of each of the "predictive" genes and radiation sensitivity. In general for each of the selected genes, a higher expression value was correlated with a more radiosensitive phenotype.

The likelihood that chance alone would be able to predict 22/35 samples correctly needed to be determined. Although, the likelihood of any predicted SF2 being correct was 20% for most samples, the fact was that not all possible SF2 values (0.01-1.0) had the same probability of being predicted by the classifier. Therefore a statistical test was generated where 10,000 permutations of incorrectly paired predicted SF2 and true SF2. Only twice in the 10,000 permutations were 22 samples classified correctly by chance alone (p=0.0002) was generated, further supporting the validity of the approach.

EXAMPLE III

Quantitative PCR validates the expression level of the three known genes selected by the analysis as predictive of radiation response. To validate the gene selection step, the inventors determined the expression level of the three known genes selected by the analysis using quantitative real-time PCR. To perform these experiments of validation, cell lines were selected for each candidate gene that were on opposing ends of the radiation sensitivity and gene expression spectrum. As shown in FIGS. 3A through F, there was excellent correlation between quantitative real-time PCR and microarrays for all three known genes selected by the analysis. A total of 26 cell lines were assayed (10 lines for RGS-19, 8 lines for RbAp48, 8 lines for Ribose 5 Phosphate Isomerase A). RT-PCR gene expression values for the gene of interest in 22 of the 26 cell lines fell within the expected range measured by the Affymetrix HU-6800 chip.

EXAMPLE IV

Figure 4:
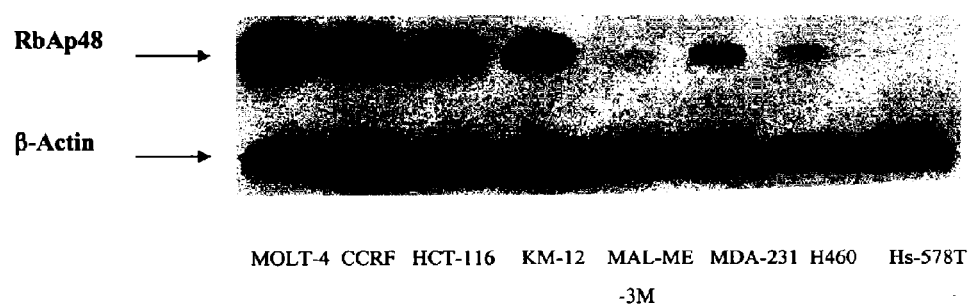
FIG. 4 is an immunublot showing that RbAp48 is highly expressed in radiosensitive but not in radioresistant cells.
Figure 5A:
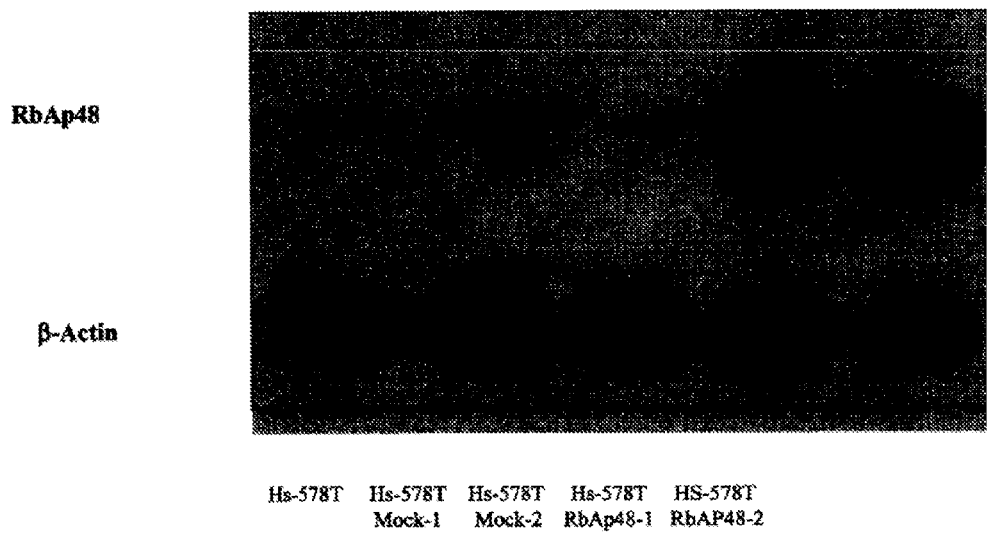
FIG. 5A is an immunoblot depicting several stable RbAp48 hi-expressors clones developed after the inventors transfected RbAp48 into HS-578T cells, a breast cancer cell line that was radioresistant and displayed low expression of RbAp48.
Figure 5B:
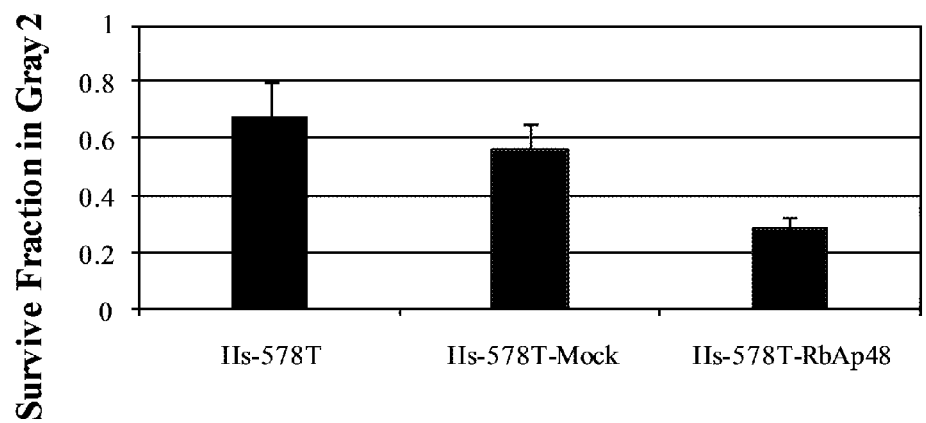
FIG. 5B is a graph showing that RbAp48 overexpression induces radiosensitization.

Overexpression of RbAp48 induces radiosensitization. RbAp48, a WD-40 protein, was first identified as a ubiquitous binding partner for the retinoblastoma protein. It has been shown that it is required for transcriptional repression of E2F-regulated genes. Furthermore, MSI1, an RbAp48 homolog in Saccharomyces cerevisiae was shown to be a negative regulator of Ras. Since both proliferation and Ras have been implicated in pathways mediating radiation resistance, the inventors hypothesized that RbAp48 could be mechanistically linked to radiation sensitivity. FIG. 4 shows that RbAp48 protein expression correlated with its RNA expression. Radiosensitive cell lines had a higher expression of this protein than radioresistant cell lines. The inventors transfected RbAp48 into HS-578T cells, a breast cancer cell line that was radioresistant and displayed low expression of RbAp48. Several stable RbAp48 hi-expressors clones were developed, as shown in FIG. 5. The clones were treated with 2Gy of radiation and assayed. Overexpression of RbAp48 conferred a radiosensitive phenotype to previously radioresistant HS-578T cells (SF2 RbAp48 hi=0.27 vs Mock=0.68), establishing a mechanisitic link between RbAp48 and radiosensitivity, thus validating the biological value of the classifier.

The present invention includes, for the first time, a genome-wide approach to the identification of potential targets for radiosensitization using a novel radiation sensitivity classifier. In thismethod a radiation sensitivity classifier is developed to predict the inherent radiosensitivity of tumor cell lines as measured by survival fraction at 2 Gy (SF2), based on gene expression profiles. This was performed in a subset of 35 cell lines from the NCI panel of 60 whose expression profiles (Affymetrix HU-6800) were available in the literature. The classifier correctly predicted within 10% the SF2 value in 22 of 35 cell lines from the NCI panel of 60, a result significantly different from chance (p=0.0002). Furthermore, the gene selection step consistently chose three known and one unknown gene as correlated with radiosensitivity prediction. The expression of these selected "predictive" genes was validated by quantitative real-time PCR, where excellent correlation between expression values as measured by qRT-PCR and microarrays was shown. Most importantly transfection of RbAp48, one of the "predictive" genes selected by the classifier, into HS-578T cells (a radioresistant and low RbAp48 expressor) induced radiosensitization, thus biologically validating the novel approach to gene analysis.

The implications of these findings are significant. First, the clinical strategy of radiosensitization using concurrent radiochemotherapy protocols has resulted in a significant increase in overall survival for lung, cervical, head and neck and esophageal cancer. However, one of the major hurdles preventing the development of better radiosensitizing agents is the lack of knowledge of targets known to affect radiation sensitivity. The technology presented herein provides for the identification of novel targets that can be exploited for therapeutic gain.

Second, it has been shown for the first time that radiation sensitivity is predictable based on baseline gene expression profiles. Although RT has been used in cancer therapeutics since the early $20^{th}$ century, the development of the clinical science has been largely empirical. As a result radiation doses are prescribed today mainly based on normal tissue tolerance and tumor control probability guidelines. These guidelines have been developed mostly over time based on historical clinical experience and retrospective clinical databases. Therefore radiation oncologists today prescribe radiation for an "average" patient with an "average" tumor without any consideration to potential individual differences in the biology of the patient and/or tumor. The observation that radiation sensitivity is predictable based on baseline gene expression profiles, represents a major leap forward from this view and may open the door to radiation dose individualization and tailoring.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be the to fall therebetween. Now that the invention has been described,

What is claimed is:

1. A method of generating a radiation classifier for determining cellular irradiation survival before exposure to the radiation in a carcinoma, glioma, melanoma, or adenocarcinoma comprising the steps of:
   establishing at least one survival fraction value of at least one cell line, wherein the one survival fraction value is established by determining the survival fraction of at least one cell line after exposure to 2 Gy of radiation, and wherein the survival fraction is defined as a continuous variable;
   establishing baseline gene expression profiles from the at least one cell line absent radiation exposure;
   selecting genes further comprising:
      correlating the baseline gene expression profiles of the at least one cell line with the cell survival fraction value to select genes indicative of cellular radiation survival using Significant Analysis of Microarrays; and applying the gene expression of the carcinoma, glioma, melanoma, or adenocarcinoma to the genes indicative of cellular survival fraction values to determine the cellular radiation survival of the carcinoma, glioma, melanoma, or adenocarcinoma using a linear regression model.

2. The method of claim 1 wherein baseline gene expression from the at least one cell line is established from a microarray.

3. The method of claim 1 further comprising
obtaining gene expression from a cancer or tumor prior to irradiation; and
comparing the quantitative gene expression from a cancer or tumor to the linear regression model, wherein the regression model provides a quantitative measure of the cellular radiation survival before exposure to radiation.

4. The method of claim 1 further comprising
dividing the at least one cell line data into a sample set and a test set, wherein the test set consists of one cell line;
generating the radiation classifier for determining cellular irradiation survival before exposure to the radiation using the sample set; and
evaluating the classifier using leave-one-out cross-validation.

* * * * *

UNITED STATES PATENT AND TRADEMARK OFFICE
CERTIFICATE OF CORRECTION

PATENT NO. : 7,879,545 B2
APPLICATION NO. : 10/904326
DATED : February 1, 2011
INVENTOR(S) : Javier F. Torres-Roca et al.

Page 1 of 1

It is certified that error appears in the above-identified patent and that said Letters Patent is hereby corrected as shown below:

Column 1, Lines 12 through Line 17 should read:
STATEMENT OF GOVERNMENT INTEREST
This invention was made with government support under grant numbers CA108926, CA085052, CA085429, and CA098522 awarded by the National Institutes of Health. The Government has certain rights in the invention.

Signed and Sealed this
Thirteenth Day of August, 2019

Andrei Iancu
*Director of the United States Patent and Trademark Office*